(12) United States Patent
Fukunaga et al.

(10) Patent No.: US 8,198,437 B2
(45) Date of Patent: *Jun. 12, 2012

(54) 6-PYRIMIDINYL-PYRIMID-4-ONE DERIVATIVE

(75) Inventors: Kenji Fukunaga, Kanagawa (JP); Kazutoshi Watanabe, Toyko (JP); Pascal Barneoud, Paris (FR); Jesus Benavides, Paris (FR); Jeremy Pratt, Paris (FR)

(73) Assignees: Mitsubishi Tanabe Pharma Corporation, Osaka (JP); Sanofi-Aventis, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/677,213

(22) PCT Filed: Sep. 12, 2008

(86) PCT No.: PCT/JP2008/066936
§ 371 (c)(1),
(2), (4) Date: Oct. 7, 2010

(87) PCT Pub. No.: WO2009/035162
PCT Pub. Date: Mar. 19, 2009

(65) Prior Publication Data
US 2011/0021773 A1 Jan. 27, 2011

(30) Foreign Application Priority Data

Sep. 14, 2007 (JP) .................... 2007-269485
Sep. 25, 2007 (JP) .................... 2007-275713
Jan. 11, 2008 (EP) ..................... 08290028

(51) Int. Cl.
*C07D 413/00* (2006.01)
(52) U.S. Cl. ..................... 544/123; 514/235.8
(58) Field of Classification Search .................. 544/101, 544/296, 295, 320, 123; 514/235.8
See application file for complete search history.

(56) References Cited

U.S. PATENT DOCUMENTS

| 7,427,615 B2 * | 9/2008 | Uehara et al. ............. 514/229.5 |
| 7,504,411 B2 * | 3/2009 | Watanabe et al. ............. 514/273 |
| 7,572,793 B2 * | 8/2009 | Uehara et al. ............. 514/235.8 |
| 2005/0130967 A1 | 6/2005 | Uehara et al. |
| 2009/0124618 A1 * | 5/2009 | Watanabe et al. .......... 514/235.5 |
| 2009/0239864 A1 * | 9/2009 | Watanabe et al. .......... 514/235.8 |
| 2010/0113775 A1 * | 5/2010 | Watanabe et al. ............. 544/123 |

FOREIGN PATENT DOCUMENTS

| CN | 1555367 A | 12/2004 |
| EP | 0 616 032 | 9/1994 |
| WO | 03/027080 | 4/2003 |
| WO | WO 03027080 A1 * | 4/2003 |
| WO | 2006/036015 A2 | 4/2006 |
| WO | 2006/036015 A3 | 4/2006 |
| WO | 2007/119463 | 10/2007 |

OTHER PUBLICATIONS

International Search Report that issued with respect to PCT/JP2008/066936, mailed Jun. 11, 2008.
International Preliminary Report on Patentability for PCT/JP2008/066936, mailed Mar. 25, 2010.

* cited by examiner

*Primary Examiner* — James O Wilson
*Assistant Examiner* — Alexander R Pagano
(74) *Attorney, Agent, or Firm* — Greenblum & Bernstein, P.L.C.

(57) ABSTRACT

A compound represented by the formula (I) or a pharmaceutically acceptable salt thereof:

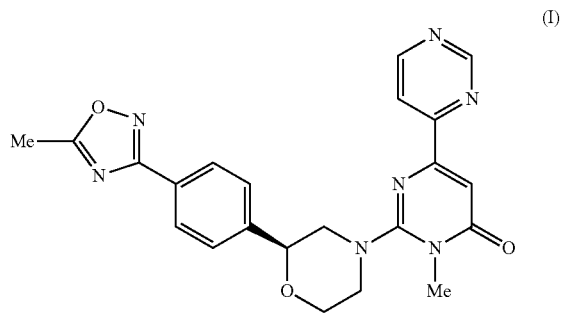

(I)

which is used for preventive and/or therapeutic treatment of a disease caused by abnormal activity of tau protein kinase 1 such as a neurodegenerative diseases (e.g. Alzheimer disease).

3 Claims, No Drawings

6-PYRIMIDINYL-PYRIMID-4-ONE DERIVATIVE

TECHNICAL FIELD

The present invention relates to compounds that are useful as an active ingredient of a medicament for preventive and/or therapeutic treatment of diseases mainly caused by abnormal activity of tau protein kinase 1 (TPK1 also called GSK3beta glycogen synthase kinase 3 beta), such as neurodegenerative diseases (e.g. Alzheimer disease).

BACKGROUND ART

Alzheimer disease is progressive senile dementia, in which marked cerebral cortical atrophy is observed due to degeneration of nerve cells and decrease of nerve cell number. Pathologically, numerous senile plaques and neurofibrillary tangles are observed in brain. The number of patients has been increased with the increment of aged population, and the disease arises a serious social problem. Although various theories have been proposed, a cause of the disease has not yet been elucidated. Early resolution of the cause has been desired.

It has been known that the degree of appearance of two characteristic pathological changes of Alzheimer disease well correlates to the degree of intellectual dysfunction. Therefore, researches have been conducted from early 1980's to reveal the cause of the disease through molecular level investigations of components of the two pathological changes. Senile plaques accumulate extracellularly, and β amyloid protein has been elucidated as their main component (abbreviated as "A β" hereinafter in the specification: Biochem. Biophys. Res. Commun., 120, 885 (1984); EMBO J., 4, 2757 (1985); Proc. Natl. Acad. Sci. USA, 82, 4245 (1985)). In the other pathological change, i.e., the neurofibrillary tangles, a double-helical filamentous substance called paired helical filament (abbreviated as "PHF" hereinafter in the specification) accumulate intracellularly, and tau protein, which is a kind of microtubule-associated protein specific for brain, has been revealed as its main component (Proc. Natl. Acad. Sci. USA, 85, 4506 (1988); Neuron, 1, 827 (1988)).

Furthermore, on the basis of genetic investigations, presenilins 1 and 2 were found as causative genes of familial Alzheimer disease (Nature, 375, 754 (1995); Science, 269, 973 (1995); Nature. 376, 775 (1995)), and it has been revealed that presence of mutants of presenilins 1 and 2 promotes the secretion of Aβ (Neuron, 17, 1005 (1996); Proc. Natl. Acad. Sci. USA, 94, 2025 (1997)). From these results, it is considered that, in Alzheimer disease, Aβ abnormally accumulates and agglomerates due to a certain reason, which engages with the formation of PHF to cause death of nerve cells. It is also expected that extracellular outflow of glutamic acid and activation of glutamate receptor responding to the outflow may possibly be important factors in an early process of the nerve cell death caused by ischemic cerebrovascular accidents.

It has been reported that kainic acid treatment that stimulates the AMPA receptor, one of glutamate receptor, increases mRNA of the amyloid precursor protein (abbreviated as "APP" hereinafter in the specification) as a precursor of Aβ (Society for Neuroscience Abstracts, 17, 1445 (1991)), and also promotes metabolism of APP (The Journal of Neuroscience, 10, 2400 (1990)). Therefore, it has been strongly suggested that the accumulation of Aβ is involved in cellular death due to ischemic cerebrovascular disorders. Other diseases in which abnormal accumulation and agglomeration of Aβ are observed include, for example, Down syndrome, cerebral bleeding due to solitary cerebral amyloid angiopathy, Lewy body disease and the like. Furthermore, as diseases showing neurofibrillary tangles due to the PHF accumulation, examples include progressive supranuclear palsy, subacute sclerosing panencephalitic parkinsonism, postencephalitic parkinsonism, pugilistic encephalitis, Guam parkinsonism-dementia complex, Lewy body disease and the like.

The tau protein is generally composed of a group of related proteins that forms several bands at molecular weights of 48-65 kDa in SDS-polyacrylamide gel electrophoresis, and it promotes the formation of microtubules. It has been verified that tau protein incorporated in the PHF in the brain suffering from Alzheimer disease is abnormally phosphorylated compared with usual tau protein (J. Biochem., 99, 1807 (1986); Proc. Natl. Acad. Sci. USA, 83, 4913 (1986)). An enzyme catalyzing the abnormal phosphorylation has been isolated. The protein was named as tau protein kinase 1 (abbreviated as "TPK1" hereinafter in the specification), and its physicochemical properties have been elucidated (J. Biol. Chem., 267, 10897 (1992)). Moreover, cDNA of rat TPK1 was cloned from a rat cerebral cortex cDNA library based on a partial amino acid sequence of TPK1, and its nucleotide sequence was determined and an amino acid sequence was deduced. As a result, it has been revealed that the primary structure of the rat TPK1 corresponds to that of the enzyme known as rat GSK-3β (glycogen synthase kinase 3β, FEBS Lett., 325, 167 (1993)).

It has been reported that Aβ, the main component of senile plaques, is neurotoxic (Science, 250, 279 (1990)). However, various theories have been proposed as for the reason why Aβ causes the cell death, and any authentic theory has not yet been established. Takashima et al. observed that the cell death was caused by Aβ treatment of fetal rat hippocampus primary culture system, and then found that the TPK1 activity was increased by Aβ treatment and the cell death by Aβ was inhibited by antisense of TPK1 (Proc. Natl. Acad. Sci. USA, 90, 7789 (1993); EP616032).

In view of the foregoing, compounds which inhibit the TPK1 activity may possibly suppress the neurotoxicity of Aβ and the formation of PHF and inhibit the nerve cell death in the Alzheimer disease, thereby cease or defer the progress of the disease. The compounds may also be possibly used as a medicament for therapeutic treatment of ischemic cerebrovascular disorder, Down syndrome, cerebral amyloid angiopathy, cerebral bleeding due to Lewy body disease and the like by suppressing the cytotoxicity of Aβ. Furthermore, the compounds may possibly be used as a medicament for therapeutic treatment of neurodegenerative diseases such as progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration and frontotemporal dementia, vascular dementia, traumatic injuries, brain and spinal cord trauma, peripheral neuropathies, retinopathies and glaucoma, as well as other diseases such as non-insulin dependent diabetes, obesity, manic depressive illness, schizophrenia, alopecia, breast cancer, non-small cell lung carcinoma, thyroid cancer, T or B-cell leukemia, and several virus-induced tumors.

Inhibitors of human TPK1 may also inhibit pfGSK3, an ortholog of this enzyme found in *Plasmodium falciparum*, as a consequence they could be used for the treatment of malaria (Biochimica et Biophysica Acta 1697, 181-196, 2004).

Recently, both human genetics and animal studies have pointed out the role of Wnt/LPR5 pathway as a major regulator of bone mass accrual. Inhibition of TPK1 leads to the consequent activation of canonical Wnt signalling. Because deficient Wnt signalling has been implicated in disorders of reduced bone mass, TPK1 inhibitors may also be used for treating disorders of reduced bone mass, bone-related pathologies, osteoporosis.

According to recent data, TPK1 inhibitors might be used in the treatment or prevention of *Pemphigus vulgaris*.

Recent studies show that TPK1 inhibitor treatment improves neutrophil and megakaryocyte recovery. Therefore, TPK1 inhibitors will be useful for the treatment of neutropenia induced by cancer chemotherapy.

Some 6-pyrimidinyl-pyrimid-2-one derivatives are already known to be active as TPK1 inhibitors (WO03/027080), nevertheless, it has been surprisingly found that the compound of formula (I) present a better in vivo activity without inhibition of cytochrome P450 2D6 CYP 2D6. This will contribute significantly to the develop ability of the compound.

Further, it is generally essential that compounds used as a medicine are studied in view of a combined administration with other drugs. This is increasing with recent diversification of medical treatment and aging of society. In order to avoid drug-drug interactions it is hoped that, for instance, one of the compounds administered does not inhibit cytochrome P450 enzymes, such as cytochrome P450 2D6. This could lead to unpredictable side effects related to the drug combination.

From the known compounds of WO03/027080, the in vitro activities were comparable and therefore it was expected that all these compounds would have a similar profile. Surprisingly, it was found that one of the compounds generically covered but not exemplified in WO03/027080 was significantly different from the other disclosed compounds.

DISCLOSURE OF THE INVENTION

An object of the present invention is to provide a compound useful as an active ingredient of a medicament for preventive and/or therapeutic treatment of diseases such as Alzheimer disease, with improved in vivo activity without inhibition of cytochrome 2D6. More specifically, the object is to provide a novel compound useful as an active ingredient of a medicament that enables radical prevention and/or treatment of the neurodegenerative diseases such as Alzheimer disease by inhibiting the TPK1 activity to suppress the neurotoxicity of A and the formation of the PHF and by inhibiting the death of nerve cells with improved in vivo activity without inhibition of CYP 2D6.

It was surprisingly found that a novel compound represented by the following formula (I) had the desired activity and were useful as an active ingredient of a medicament for preventive and/or therapeutic treatment of the aforementioned diseases. The present invention was achieved on the basis of these findings.

The present invention thus provides a compound represented by the formula (I):

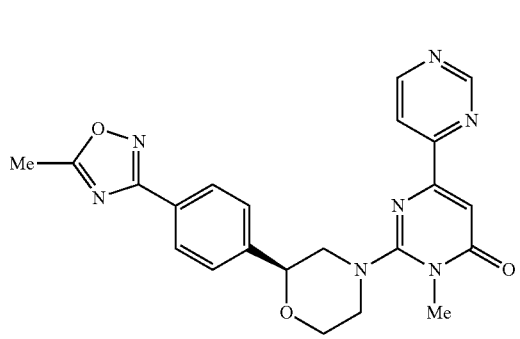

(I)

{3-Methyl-2-((2S)-2-(4-(5-methyl-1,2,4-oxadiazol-3-yl) phenyl)morpholino)-6-(pyrimidin-4-yl)pyrimidin-4(3H)-one} or a pharmaceutically acceptable salt thereof.

The present invention relates to 3-Methyl-2-((2S)-2-(4-(5-methyl-1,2,4-oxadiazol-3-yl)phenyl)morpholino)-6-(pyrimidin-4-yl)pyrimidin-4(3H)-one or a pharmaceutically acceptable salt as a medicament.

The present invention relates to 3-Methyl-2-((2S)-2-(4-(5-methyl-1,2,4-oxadiazol-3-yl)phenyl)morpholino)-6-(pyrimidin-4-yl)pyrimidin-4(3H)-one or a pharmaceutically acceptable salt as a tau protein kinase 1 inhibitor.

The present invention relates to 3-Methyl-2-((2S)-2-(4-(5-methyl-1,2,4-oxadiazol-3-yl)phenyl)morpholino)-6-(pyrimidin-4-yl)pyrimidin-4(3H)-one or a pharmaceutically acceptable salt as a medicament used for preventive and/or therapeutic treatment of a disease caused by tau protein kinase 1 hyperactivity.

The present invention relates to 3-Methyl-2-((2S)-2-(4-(5-methyl-1,2,4-oxadiazol-3-yl)phenyl)morpholino)-6-(pyrimidin-4-yl)pyrimidin-4(3H)-one or a pharmaceutically acceptable salt for preventive and/or therapeutic treatment of a neurodegenerative disease.

The present invention relates to 3-Methyl-2-((2S)-2-(4-(5-methyl-1,2,4-oxadiazol-3-yl)phenyl)morpholino)-6-(pyrimidin-4-yl)pyrimidin-4(3H)-one or a pharmaceutically acceptable salt for preventive and/or therapeutic treatment of Alzheimer disease, ischemic cerebrovascular accidents, Down syndrome, cerebral bleeding due to cerebral amyloid angiopathy, progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration, frontotemporal dementia, vascular dementia, traumatic injuries, brain and spinal cord trauma, peripheral neuropathies, retinopathies and glaucoma.

The present invention relates to 3-Methyl-2-((2S)-2-(4-(5-methyl-1,2,4-oxadiazol-3-yl)phenyl)morpholino)-6-(pyrimidin-4-yl)pyrimidin-4(3H)-one or a pharmaceutically acceptable salt for preventive and/or therapeutic treatment of a disease selected from the group consisting of non-insulin dependent diabetes, obesity, manic depressive illness, schizophrenia, alopecia, breast cancer, non-small cell lung carcinoma, thyroid cancer, T or B-cell leukemia, osteoporosis, malaria, neutropenia induced by cancer chemotherapy and a virus-induced tumor.

Previous studies have shown that GSK3 activity decreases Long Term Potentiation, a electrophysiological correlate of memory consolidation, suggesting that inhibitor of this enzyme may have procognitive activity. Procognitive effects of the compound could find application for the treatment of memory deficits characteristic of Alzheimer's disease, Parkinson disease, age associated memory impairment, mild cognitive impairment, brain trauma, schizophrenia and other conditions in which such deficits are observed.

The present invention relates to the formula (I) 3-Methyl-2-((2S)-2-(4-(5-methyl-1,2,4-oxadiazol-3-yl)phenyl)morpholino)-6-(pyrimidin-4-yl)pyrimidin-4(3H)-one or a pharmaceutically acceptable salt for therapeutic treatment of a disease characterized by cognitive and memory deficits characteristic of Alzheimer's disease, Parkinson's disease, age-associated memory impairment, mild cognitive impairment, brain trauma, schizophrenia and other conditions in which such deficits are observed.

MODE FOR CARRYING OUT THE INVENTION

Unless otherwise indicated, the following definitions are set forth to illustrate and defined the meaning and scope of the various terms used to describe the invention herein.

The pharmaceutically acceptable salt of the compound represented by the aforementioned formula (I) may include the salt with inorganic acid such as hydrochloric acid, hydrobromic acid and the like and the salt with organic acid such as acetic acid, propionic acid, tartaric acid, fumaric acid, maleic acid, malic acid, oxalic acid, succinic acid, citric acid, benzoic acid and the like.

In addition to the compound represented by the aforementioned formula (I), a pharmaceutically acceptable salt thereof, their solvates and hydrates also fall within the scope of the present invention.

The compounds of the present invention have inhibitory activity in vivo against TPK1. Therefore, they can inhibit TPK1 activity in patients of neurodegenerative diseases such as Alzheimer disease, thereby suppress the neurotoxicity of Aβ and the formation of PHF and inhibit the nerve cell death. Accordingly, the compounds of the present invention are useful as an active ingredient of a medicament which radically enables preventive and/or therapeutic treatment of Alzheimer disease. In addition, the compounds of the present invention are also useful as an active ingredient of a medicament for preventive and/or therapeutic treatment of ischemic cerebrovascular accidents, Down syndrome, cerebral bleeding due to solitary cerebral amyloid angiopathy, progressive supranuclear palsy, subacute sclerosing panencephalitis, postencephalitic parkinsonism, pugilistic encephalosis, Guam parkinsonism-dementia complex, Lewy body disease, Pick's disease, corticobasal degeneration frontotemporal dementia, vascular dementia, traumatic injuries, brain and spinal cord trauma, peripheral neuropathies, retinopathies and glaucoma, non-insulin dependent diabetes, obesity, manic depressive illness, schizophrenia, alopecia, breast cancer, non-small cell lung carcinoma, thyroid cancer, T or B-cell leukemia, and several virus-induced tumors, osteoporosis, malaria, neutropenia induced by cancer chemotherapy, and a disease characterized by cognitive and memory deficits characteristic of Alzheimer's disease, Parkinson's disease, age-associated memory impairment, mild cognitive impairment, brain trauma, schizophrenia and other conditions in which such deficits are observed.

The compound of the present invention also has low inhibitory activity on CYP2D6, causing less effect on the metabolism of the medicament to be used in combination. Therefore, the side effect is hardly produced from medicament-medicament interactions even when the medicament is used in combination with other medicaments.

Further, the compound of the present invention presents no significant toxicities and thus is suitable to be used in a medicament.

As the active ingredient of the medicament of the present invention, a substance may be used which represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more of pharmaceutical additives. As the active ingredient of the medicament of the present invention, two or more of the aforementioned substance may be used in combination.

A type of the pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like.

Dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 3000 mg (the weight of an active ingredient) to an adult.

EXAMPLES

The present invention will be explained more specifically with reference to examples. However, the scope of the present invention is not limited to the following examples.

Preparation of the Compound of the Present Invention

Example 1

3-Methyl-2-((2S)-2-(4-(5-methyl-1,2,4-oxadiazol-3-yl)phenyl)morpholino)-6-(pyrimidin-4-yl)pyrimidin-4(3H)-one The compound of the present invention is prepared by the condensation with 2-chloro-1-methyl-1H-[4,4']bipyrimidinyl-6-one (intermediate 1) and corresponding amines (intermediate 19) with the existence of base.

General synthetic scheme of the compound of the present invention is as follows.

Scheme 1: Synthetic scheme of intermediate 1

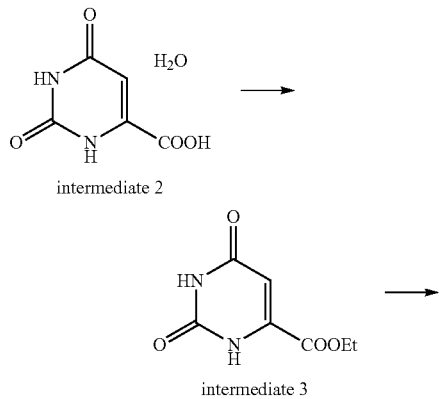

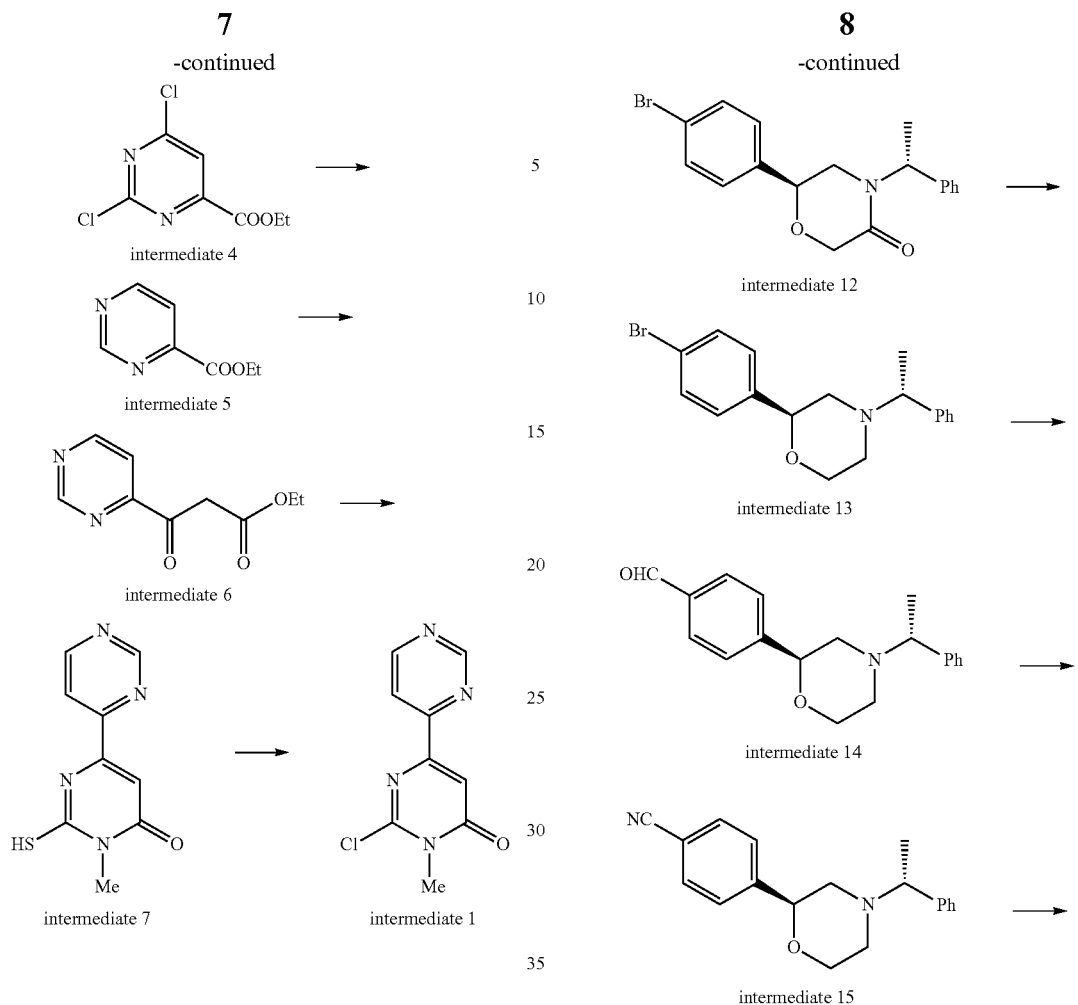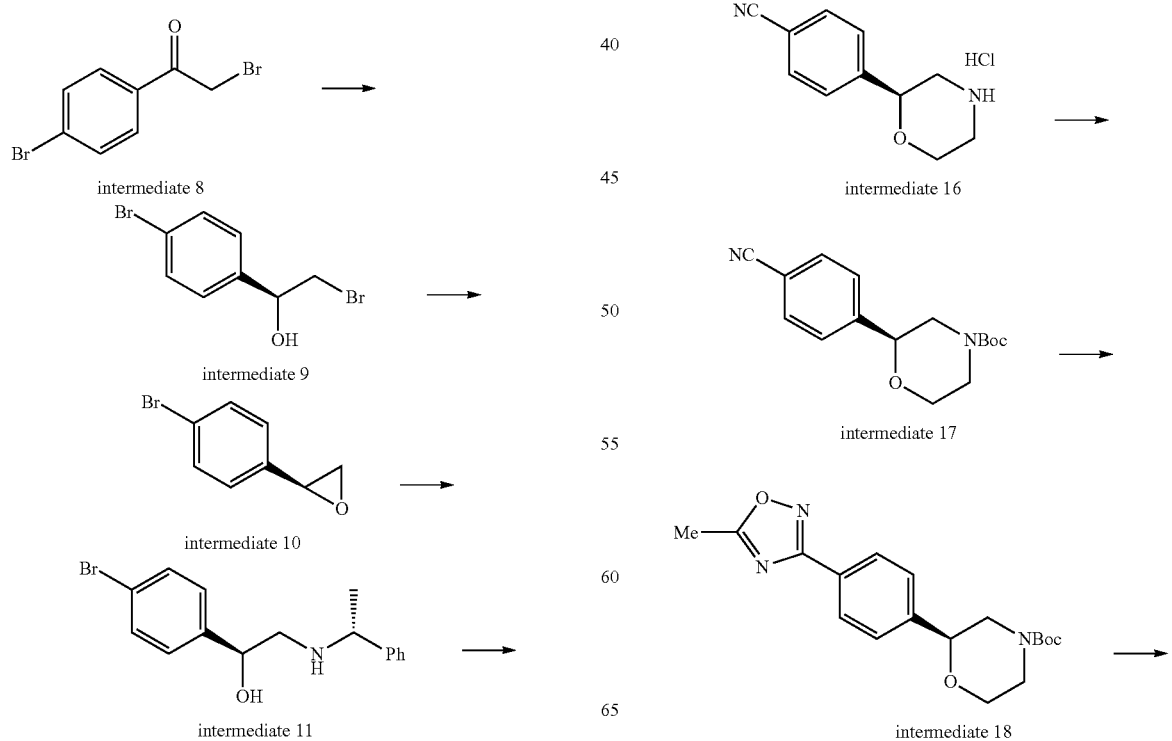

-continued

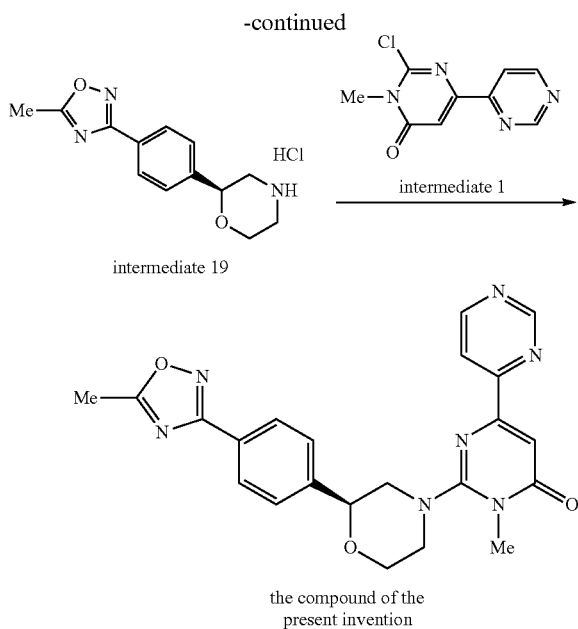

intermediate 19 + intermediate 1 → the compound of the present invention

Step 1-1: Ethyl Orotate (Intermediate 3)

Orotic acid monohydrate (intermediate 2, 53.19 g, 0.306 mmol) was added to a solution of 1,8-diazabicyclo[5.4.0]undec-7-ene (46.51 g, 0.306 mmol) in dimethylformamide (85 ml). After the solution was stirred for 5 minutes, ethyl iodide (57.14 g, 0.366 mmol) was added to the solution and the mixture was heated at 60° C. for 5 hours. Water (1000 ml) was added to the mixture, and the resulting precipitate was collected by filtration, washed with water, and dried to give ethyl orotate (intermediate 3, 49.25 g, 88%).
$^1$H NMR (DMSO-d$_6$) δ: 1.29 (3H, dt, J=1.5, 6.9 Hz), 4.31 (2H, dq, J=1.2, 7.2 Hz), 6.04 (1H, d, J=1.2 Hz), 11.11 (1H, s), 11.37 (1H, s)
MS: [M+H]$^+$=185
Melting point: 205.5° C.

Step 1-2: Ethyl 2,6-dichloropyrimidine-4-carboxylate (Intermediate 4)

N,N-Diethylaniline (60 ml, 0.377 mmol) was added to a mixture of ethyl orotate (intermediate 3, 97.70 g, 0.531 mmol) and phosphorus oxychloride (120 ml, 1.31 mol) and the mixture was refluxed for 70 minutes. The solution was poured into ice water, and the resulting solid was collected by filtration and washed with water. This solid was dissolved in ethyl acetate, and the solution was filtered through silica gel. The filtrate was dried over sodium sulfate, and concentrated under reduced pressure. The obtained residue was purified by short silica gel column chromatography (eluent; hexane/ethyl acetate=2/1) to give ethyl 2,6-dichloropyrimidine-4-carboxylate (intermediate 4, 99.94 g, 85%).
$^1$H NMR (CDCl$_3$) δ: 1.45 (3H, t, J=7.3 Hz), 4.51 (3H, q, J=7.1 Hz), 7.97 (1H, s)
MS: [M+H]$^+$=221
Melting point: 31.6° C.

Step 1-3: Ethyl Pyrimidine-4-carboxylate (Intermediate)

Triethylamine (48.03 g, 0.475 mmol) was added to a solution of ethyl 2,6-dichloropyrimidine-4-carboxylate (intermediate 4, 38.60 g, 0.175 mmol) in tetrahydrofuran (700 ml). The solution was added with Palladium-carbon (5%), and stirred under a hydrogen atmosphere for 6 hours. The solid in the reaction system was removed by filtration, and the filtrate was concentrated under reduced pressure. The obtained residue was purified by silica gel column chromatography to give ethyl pyrimidine-4-carboxylate (intermediate 5, 23.06 g, 87%).
$^1$H NMR (CDCl$_3$) δ: 1.46 (3H, t, J=7.1 Hz), 4.52 (2H, q, J=7.1 Hz), 8.03 (1H, dd, J=1.7, 5.0 Hz), 9.00 (1H, d, J=5.0 Hz), 9.42 (1H, d, J=1.4 Hz)
MS: [M+H]$^+$=153
Melting point: 36.8° C.

Step 1-4: Ethyl 3-oxo-3-(pyrimidin-4-yl)propionate (Intermediate)

A solution of ethanol (16.18 g, 0.351 mol) in diethyl ether (15 ml) was added to a solution of sodium hydride (13.71 g, 0.343 mol, 60% in paraffin, paraffin was removed by washing with hexane) in diethyl ether (100 ml). After stirring the mixture for 30 minutes, the solvent was evaporated under reduced pressure, and toluene (100 ml) was added to the residue. The solution was added with a solution of ethyl pyrimidine-4-carboxylate (intermediate 5, 30.86 g, 0.203 mol) and ethyl acetate (30.48 g, 0.346 mol) in toluene (100 ml), and the mixture was heated at 80° C. for 3 hours. The mixture was added with hydrochloric acid and then sodium bicarbonate to be adjusted to pH 4. The solution was partitioned between water and ethyl acetate. The organic layer was washed with brine and dried over sodium sulfate. The solvent was evaporated under reduced pressure to give ethyl 3-oxo-3-(pyrimidin-4-yl) propionate (intermediate 6, 36.10 g, 92%).
$^1$H NMR (CDCl$_3$) δ: 1.35 (3H, t, J=6.9 Hz), 4.31 (2H, q, J=7.2 Hz), 6.47 (1H, s), 7.84 (1H, dd, J=1.5, 5.4 Hz), 8.89 (1H, d, J=5.1 Hz), 9.24 (1H, d, J=1.2 Hz), 12.22 (1H, s)
MS: [M+H]$^+$=195
Melting point: 52.3° C.

Step 1-5: 2-Mercapto-1-methyl-1H-[4,4']bipyrimidinyl-6-one (Intermediate 7)

A solution of ethyl 3-oxo-3-(pyrimidin-4-yl)propionate (intermediate 6, 36.10 g, 0.186 mol), N-methylthiourea (25.40 g, 0.282 mol) and 1,8-diazabicyclo[5.4.0]undec-7-ene (29.11 g, 0.191 mol) in ethanol (150 ml) was refluxed for 21 hours. A half amount of ethanol was evaporated under reduced pressure and hydrochloric acid was added. The resulting precipitate was collected by filtration, washed with water and dried. The precipitate was stirred in hot ethyl acetate (1000 ml), and the precipitate was collected by filtration and dried to give 2-mercapto-1-methyl-1,3-[4,4]bipyrimidinyl-6-one (intermediate 7, 33.91 g, 83%).
$^1$H NMR (CDCl$_3$) δ: 3.59 (3H, s), 6.91 (1H, s), 8.27 (1H, d, J=2.4 Hz), 9.08 (1H, d, J=2.1 Hz), 9.41 (1H, s), 11.99 (1H, s)
MS: [M+H]$^+$=221
Melting point: 228.0° C. (decomp.)

Step 1-6: 2-Chloro-1-methyl-1H-[4,4]bipyrimidinyl-6-one (Intermediate 1)

A suspension of 2-mercapto-1-methyl-1H-[4,4']bipyrimidinyl-6-one (intermediate 7, 8.8 g, 40 mmol) in a mixed solvent of dimethylformamide (30 ml) and 1,2-dichloroethane (30 ml) was added to phosphorus oxychloride (11.2 ml, 120 mmol), and the mixture was stirred at 65° C. for 50 minutes. The solution was poured into ice-cooled dichloromethane (300 ml), water was added to the solution, and the mixture was vigorously stirred for 5 minutes. Aqueous sodium carbonate solution (25.4 g, 240 mmol, in water (100 ml)) was added and the pH was adjusted to 8 with saturated aqueous sodium hydrogen carbonate solution. Aqueous sodium hypochlorite solution (5% in water, 120 ml) was added. After filtration with celite, the organic layer was extracted twice with dichloromethane, and washed with saturated aqueous sodium bicarbonate solution and dried over sodium sulfate. The solvent was evaporated under reduced pressure, and the obtained residue was purified by silica gel column chromatography (eluent; ethyl acetate/hexane=1/1) and washed with diethyl ether to give 2-chloro-1-methyl-1H-[4,4']bipyrimidinyl-6-one (intermediate 1) as a pale-yellow solid (2.2 g, 62%, purity 98.7%).

$^1$H NMR (CDCl$_3$) δ: 3.74 (3H, s), 7.58 (1H, s), 8.19 (1H, d, J=5.7 Hz), 8.92 (1H, d, J=5.2 Hz), 9.31 (1H, d, J=1.1 Hz)

MS: [M+H]$^+$=223

Melting point: 168.5° C. (decomp.)

Step 1-7: 2-Bromo-(1S)-1-(4-bromophenyl)ethanol (Intermediate 9)

(S)—CBS (25 ml, (S)-2-methyl-CBS-oxazaborolidine, manufactured by Aldrich, 1.0 M solution in toluene) was cooled to 0° C., and borane-tetrahydrofuran complex (185 ml, 185 mmol, 1.0 M solution in tetrahydrofuran) was added. After the flask was cooled by ice-sodium chloride bath, a solution of 4-bromophenacyl bromide (intermediate 8, 50.28 g, 181 mmol) in dichloromethane (300 ml) was added dropwise over one hour while maintaining the temperature at −5° C. to 0° C. After stirring the mixture at 0° C. for 50 minutes, methanol (12 ml) was added by small portions. Then, 0.5 M hydrochloric acid (300 ml) was added dropwise and the mixture was stirred at room temperature for 40 minutes. The precipitate was filtered off and the filtrate was partitioned between dichloromethane and water. The organic layer was separated and the aqueous layer was extracted with methylene chloride. The organic layers were combined, washed twice with 0.5 M hydrochloric acid and brine, and dried over anhydrous sodium sulfate. The solvent was evaporated under reduced pressure to afford 2-bromo-1-(1S)-(4-bromophenyl)ethanol (intermediate 9) as a pale-brown oil. This crude product was used for next step without purification.

Step 1-8: (2S)-2-(4-Bromophenyl)oxirane (Intermediate 10)

(2S)-2-Bromo-1-(4-bromophenyl) ethanol (intermediate) obtained above was dissolved in ethyl ether (300 ml), the solution was stirred with aqueous sodium hydroxide (14.47 g, 362 mmol in 300 ml of water) in a two-layer system at room temperature for 1.5 hours. The mixture was partitioned between diethyl ether and water, and the organic layer was washed with saturated brine and dried over anhydrous sodium sulfate. The solvent was evaporated under reduced pressure to give (2S)-2-(4-bromophenyl)oxirane (intermediate 10) as a pale-brown oil. This crude product was used for next step without purification.

$^1$H-NMR (300 MHz, CDCl$_3$) δ: 2.74-2.77 (1H, m), 3.13-3.17 (1H, m), 3.82-3.84 (1H, m), 7.16 (2H, d, J=8.4 Hz), 7.48 (2H, d, J=8.4 Hz)

Step 1-9: (1S)-1-(4-bromophenyl)-2-((1R)-1-phenylethylamino)ethanol (Intermediate 11)

A mixture of (2S)-2-(4-bromophenyl)oxirane (intermediate 10) obtained above and (R)-1-phenylethylamine (65.22 g, 538 mmol) was stirred in an oil bath with heating at 80° C. for 3 hours. Excess amine was distilled off under reduced pressure (ca. 70° C. at 7 mmHg). After cooling, resulting solid residue was washed with isopropyl ether and dried to give (1S)-1-(4-bromophenyl)-2-((1R)-1-phenylethylamino) ethanol (intermediate 11, 46.76 g, 81% yield for 3 steps) as white crystals.

$^1$H-NMR (300 MHz, CDCl$_3$) δ:1.39 (3H, d, J=6.3 Hz), 2.48 (1H, dd, J=9.0 Hz, 12.0 Hz), 2.77 (1H, dd, J=3.6 Hz, 12.3 Hz), 3.82 (1H, dd, J=6.6 Hz, 13.2 Hz), 7.16 (2H, d, J=8.4 Hz), 7.20-7.27 (3H, m), 7.31-7.34 (2H, m), 7.41 (2H, d, J=8.4 Hz)

MS: [M+H]$^+$=320

Melting point: 106.3° C.

Specific optical rotation; [α]$_D$=+80.74 (c=1.0, dichloromethane)

Step 1-10: (6S)-6-(4-Bromophenyl)-4-((1R)-1-phenylethyl)morpholin-3-one (Intermediate 12)

A solution of chloroacetyl chloride (19.5 ml, 245 mmol) in dichloromethane (100 ml) was added dropwise to a ice-cooled solution of (1S)-1-(4-bromophenyl)-2-((1R)-1-phenylethylamino)ethanol (intermediate 11, 71.0 g, 222 mmol) and triethylamine (34 ml, 245 mmol) in dichloromethane (600 ml). After the mixture was stirred for 2 hours, 1 M hydrochloric acid was added and the mixture was partitioned between water and chloroform. The organic layer was washed with saturated aqueous sodium hydrogen carbonate and brine, and dried over anhydrous sodium sulfate. The solvent was evaporated under reduced pressure and the residue was dissolved in 2-propanol (600 ml). The solution was added with potassium hydroxide (85%, 18.3 g, 278 mmol). The mixture was stirred at room temperature for 15 hours. The solvent was evaporated under reduced pressure and the residue was added with ethyl acetate. The mixture was partitioned between water and ethyl acetate, and the organic layer was washed with 1 M hydrochloric acid, saturated aqueous sodium hydrogen carbonate and brine, and dried over anhydrous magnesium sulfate. The solvent was evaporated under reduced pressure to give (6S)-6-(4-bromophenyl)-4-((1R)-1-phenylethyl)morpholin-3-one (intermediate 12, 92 g) as a brown oil. This crude product was used for next reaction without purification.

$^1$H-NMR (300 MHz, CDCl$_3$) δ: 1.53 (3H, d, J=7.0 Hz), 2.96 (1H, dd, J=3.0 Hz, 12.2 Hz), 3.29 (1H, dd, J=10.8 Hz, 12.0 Hz), 4.38 (1H, d, J=16.8 Hz), 4.49 (1H, d, J=16.9 Hz), 4.53 (1H, dd, J=3.0 Hz, 10.6 Hz), 6.53 (1H, q, J=7.2 Hz), 7.14 (2H, d, J=8.3 Hz), 7.28-7.39 (5H, m), 7.45 (2H, d, J=8.4 Hz)

MS: [M+H]$^+$=360

Specific optical rotation; [α]$_D$=+71.68 (c=0.5, chloroform)

Step 1-11: (2S)-2-(4-Bromophenyl)-4-((1R)-1-phenylethyl)morpholine (Intermediate 13)

To a ice-cooled solution of (6S)-6-(4-bromophenyl)-4-((1R)-1-phenylethyl) morpholin-3-one (intermediate 12, 92 g) obtained in step 1-10 in tetrahydrofuran (400 ml) was added dropwise over 30 minutes a borane-tetrahydrofuran complex (1.0 M solution in tetrahydrofuran, 600 ml, 600 mmol). After being warmed to room temperature and stirred for 2 hours, the mixture was ice-cooled again and added dropwise with methanol (70 ml). The solvent was evaporated under reduced pressure. The residue was added with methanol (750 ml) and 1 M aqueous sodium hydroxide (280 ml). The mixture was stirred at 80° C. for one hour, during which period 1 M aqueous sodium hydroxide (70 ml) was added 3 times in every 15 minutes. After the mixture was cooled to room temperature, methanol was evaporated under reduced pressure and the resulting solution was extracted with ethyl acetate. The organic layers was washed with water and brine, and dried over anhydrous sodium sulfate. The solvent was evaporated under reduced pressure to give (2S)-2-(4-bromophenyl)-4-((1R)-1-phenylethyl)morpholine (intermediate 13, 68 g, yield 88% from intermediate 11) as white crystals.

IR(ATR):1487, 1449, 1117, 1098, 809, 758, 699, 550 cm$^{-1}$ $^1$H-NMR (CDCl$_3$) δ: 1.35 (3H, d), 2.10 (2H, m), 2.60 (1H, m), 3.05 (1H, m), 3.35 (1H, q), 3.75 (1H, m), 3.89 (1H, m), 4.55 (1H, m), 7.25 (7H, m), 7.46 (2H, d)

MS: [M+H]$^+$=346

Melting point: 88.0° C.

Specific optical rotation; [α]$_D$=+32.06 (c=1.0, dichloromethane)

Step 1-12: 4-((2S)-4-((1R)-1-Phenylethyl)morpholin-2-yl)benzaldehyde (Intermediate 14)

To a solution of (2S)-2-(4-bromophenyl)-4-((1R)-1-phenylethyl)morpholine (intermediate 13, 63.3 g, 183 mmol) in tetrahydrofuran (450 ml) was added n-butyllithium (1.57 M in hexane solution, 175 ml, 275 mmol) at −78° C. and the mixture was stirred for 20 minutes. N,N-dimethylformamide (28.3 ml 365 mmol) was added and the mixture was stirred for 2 hours at −78° C. and then allowed to be warmed to −10° C. The reaction was quenched with aqueous ammonium chloride, and the resulting solution was partitioned between water and ethyl acetate. The organic layer was washed with water and brine and dried over sodium sulfate. The solvent was evaporated under reduced pressure to afford crude 4-((2S)-4-((1R)-1-phenylethyl) morpholin-2-yl)benzaldehyde (intermediate 14, 55.1 g). This compound was used without further purification.

Step 1-13: 4-((2S)-4-((1R)-1-Phenylethyl)morpholin-2-yl)benzonitrile (Intermediate 15)

To a solution of crude 4-((2S)-4-((1R)-1-phenylethyl)morpholin-2-yl) benzaldehyde (intermediate 14, 55.1 g) in ethanol (280 ml) was added sodium acetate (30.0 g, 365 mmol) and hydroxylamine hydrochloride (25.4 g, 365 mmol) at room temperature. After a reflux for 2 hours, the mixture was partitioned between water and dichloromethane, and the organic layer was washed with water and brine and dried over sodium sulfate. The solvent was evaporated under reduced pressure. The residue was then added with acetic acid (140 ml) and acetic anhydride (140 ml). After the mixture was refluxed for 2 hours, the solvent was removed under reduced pressure. The residue was partitioned between water and chloroform. The organic layer was washed with aqueous sodium hydrogen carbonate, dried over sodium sulfate, and the solvent was removed under reduced pressure. The residue was purified by silica gel column chromatography (eluent; hexane/ethyl acetate=9/1) to afford 4-((2S)-4-((1R)-1-phenylethyl)morpholin-2-yl)benzonitrile (intermediate 15, 45.7 g, 86% from intermediate 13)

$^1$H NMR (400 MHz, CDCl$_3$) δ: 1.37 (3H, d, J=7.0 Hz), 2.01 (1H, t, J=11.0 Hz), 2.15 (1H, dt, J=3.1, 11.7 Hz), 2.60-2.65 (1H, m), 3.08-3.12 (1H, m), 3.39 (1H, q, J=7.0 Hz), 3.74 (1H, dt, J=2.4, 11.7 Hz), 3.92-3.96 (1H, m), 4.65 (1H, dd, J=2.4, 10.2), 7.24-7.35 (5H, m), 7.48 (2H, d, J=7.8 Hz), 7.63 (2H, d, J=7.8 Hz)

MS: [M+H]$^+$=293

Melting point: 83.6° C.

Specific optical rotation; [α]$_D$=+46.23 (c=0.5, chloroform)

Step 1-14: 4-((2S)-Morpholin-2-yl)benzonitrile hydrochloride (Intermediate 16)

To a solution of 4-(2S)-4-((1R)-1-phenylethyl)morpholin-2-yl)benzonitrile (intermediate 15, 45.7 g, 156 mmol) in 1,2-dichloroethane (312 ml) was added 1-chloroethyl chloroformate (66.9 g, 468 mmol) at room temperature. After a reflux for 6 hours, the solution was concentrated under reduced pressure. The residue was dissolved in methanol (312 ml) and the solution was refluxed for 2 hours. After removal of the solvent under reduced pressure, the crude product was washed with acetone and dried under reduced pressure to afford 4-((2S)-morpholin-2-yl)benzonitrile hydrochloride (intermediate 16, 27.6 g, 79%).

$^1$H NMR (400 MHz, DMSO-d$_6$) δ: 2.99 (1H, t, J=11.7 Hz), 3.12 (1H, dt, J=3.1, 12.5 Hz), 3.25-3.28 (1H, m), 3.48-3.52 (1H, m), 3.92 (1H, dt, J=2.4, 11.7 Hz), 4.15 (1H, dd, J=3.1, 12.5 Hz), 4.86 (1H, dd, J=2.4, 11.7 Hz), 7.60 (2H, d, J=8.6 Hz), 7.90 (2H, d, J=8.6 Hz), 9.37 (2H, brs)

MS: [M+H]$^+$=189

Melting point: 195.8° C.

Specific optical rotation; [α]$_D$=+30.39 (c=0.5, methanol)

Step 1-15: Tert-Butyl (2S)-2-(4-cyanophenyl)morpholine-4-carboxylate (Intermediate 17)

To a solution of 4-((2S)-morpholin-2-yl)benzonitrile Hydrochloride (intermediate 16, 17.9 g, 79.8 mmol) in tetrahydrofuran (400 ml) was added triethylamine (24.2 g, 240 mmol) and di-tert-butyl dicarbonate (19.2 g, 87.8 mmol) at 0° C. and the mixture was stirred at room temperature for 3 hours. The resulting solution was partitioned between water and ethyl acetate, and the organic layer was washed with brine, dried over sodium sulfate, and removed under reduced pressure. The residue was purified by silica gel column chromatography (eluent; hexane/ethyl acetate=6/1) to afford tert-butyl (2S)-2-(4-cyanophenyl)morpholine-4-carboxylate (intermediate 17, 17.6 g, 77%)

$^1$H NMR (400 MHz, CDCl$_3$) δ: 1.49 (9H, s), 2.69-2.80 (1H, m), 3.00-3.09 (1H, m), 3.65-3.72 (1H, m), 3.90-4.23 (3H,m), 4.48 (1H, d, J=11.0 Hz), 7.50 (2H, d, J=7.8 Hz), 7.66 (2H, d, J=7.8 Hz)

MS: [M+H]$^+$=289

Melting point: 104.2° C.

Specific optical rotation; [α]$_D$=−37.35 (c=0.5, chloroform)

Step 1-16: Tert-Butyl (2S)-2-(4-(5-methyl-1,2,4-oxadiazol-3-yl)phenyl)morpholine-4-carboxylate (Intermediate 18)

To a solution of tert-butyl (2S)-2-(4-cyanophenyl)morpholine-4-carboxylate (intermediate 17, 17.6 g, 61.1 mmol) and hydroxylamine hydrochloride (12.8 g, 183 mmol) in ethanol (120 ml) was added sodium carbonate (32.4 g, 305 mmol) in water (120 ml) at room temperature and the mixture was stirred at 80° C. for 3 hours. After removal of the solvent under reduced pressure, the residue was partitioned between water and ethyl acetate. The organic layer was washed with brine and dried over sodium sulfate. The solvent was evaporated under reduced pressure. The residue was added with xylene (150 ml) and N,N-dimethylacetamide dimethylacetal (18.1 g, 122 mmol). After the solution was refluxed for 2 hours, water was azeotropically removed using a Dean-Stark water separator with molecular sieves 4A. The mixture was concentrated under reduced pressure, and the residue was purified by silica gel column chromatography (eluent; hexane/ethyl acetate=3/1) to afford tert-butyl (2S)-2-(4-(5-methyl-1,2,4-oxadiazol-3-yl)phenyl)-morpholine-4-carboxylate (intermediate 18, 16.9 g, 80%)

$^1$H NMR (400 MHz, CDCl$_3$) δ: 1.49 (9H, s), 2.66 (3H, s), 2.77-2.90 (1H, m), 3.02-3.11 (1H, m), 3.67-3.74 (1H, m), 3.89-4.25 (3H, m), 4.48 (1H, d, J=11.0 Hz), 7.50 (2H, d, J=7.8 Hz), 8.00 (2H, d, J=7.8 Hz)

MS: [M+H]$^+$=246 (-tert-BuOCO)
Melting point: 114.4° C.
Specific optical rotation; [α]$_D$=−34.93 (c=0.5, chloroform)

Step 1-17: (2S)-2-(4-(5-Methyl-1,2,4-oxadiazol-3-yl)phenyl)morpholine Hydrochloride (Intermediate 19)

To a solution of tert-butyl (2S)-2-(4-(5-methyl-1,2,4-oxadiazol-3-yl)phenyl) morpholine-4-carboxylate (intermediate 18, 16.9 g, 49.0 mmol) in ethyl acetate (60 ml) was added 4N hydrogen chloride in ethyl acetate (150 ml) at room temperature and the solution was stirred for 3 hours. The solvent was evaporated under reduced pressure, and the resulting precipitate was filtered, washed with ethyl acetate, and dried under reduced pressure to afford (2S)-2-(4-(5-methyl-1,2,4-oxadiazol-3-yl)phenyl)morpholine hydrochloride (intermediate 19, 13.3 g, 96%).

$^1$H NMR (400 MHz, DMSO-d$_6$) δ: 2.67 (3H, s), 3.00 (1H, t, J=12.5 Hz), 3.12 (1H, dt, J=3.9 12.5 Hz), 3.27 (1H, d, J=12.5 Hz), 3.48 (1H, d, J=12.5 Hz), 3.97 (1H, dt, J=2.4, 12.5 Hz), 4.15 (1H, dd, J=3.1, 12.5 Hz), 4.89 (1H, dd, J=1.6, 11.0 Hz), 7.58 (2H, d, J=8.6 Hz), 8.03 (2H, d, J=8.6 Hz), 9.62 (2H, brs)

MS: [M+H]$^+$=246
Melting point: 286.8° C.
Specific optical rotation; [α]$_D$=+29.98 (c=0.5, methanol)

Step 1-18: 3-Methyl-2-((2S)-2-(4-(5-methyl-1,2,4-oxadiazol-3-yl)phenyl)morpholino)-6-(pyrimidin-4-yl)pyrimidin-4(3H)-one (the Compound of the Present Invention)

To a solution of 2-chloro-3-methyl-6-(pyrimidin-4-yl)-3H-pyrimidin-4-one (9.80 g, 44.0 mmol) and (2S)-2-(4-(5-methyl-1,2,4-oxadiazol-3-yl)phenyl)morpholine hydrochloride (13.3 g, 47.2 mmol) was added triethylamine (13.4 g, 132 mmol) at room temperature, and the solution was stirred at room temperature for 4 hours. After the solution was concentrated under reduced pressure, the resulting crude product was washed with water, dried under reduced pressure to afford 3-methyl-2-((2S)-2-(4-(5-methyl-1,2,4-oxadiazol-3-yl)phenyl)morpholino)-6-(pyrimidin-4-yl)pyrimidin-4(3H)-one (the compound of the present invention, 18.0 g, 89%).

$^1$H NMR (400 MHz, DMSO-d$_6$) δ: 2.68 (3H, s), 3.04 (1H, dd, J=11.0, 13.3 Hz), 3.21 (1H, dt, J=3.1 12.5 Hz), 3.49 (3H, s), 3.73 (1H, d, J=13.3 Hz), 3.80-3.85 (1H, m), 3.94 (1H, dt, J=2.3, 11.7 Hz), 4.11 (1H, dd, J=1.6, 11.7 Hz), 4.86 (1H, dd, J=2.4, 10.2 Hz), 7.02 (1H, s), 7.66 (2H, d, J=7.8 Hz), 8.03 (2H, d, J=7.8 Hz), 8.22 (1H, dd, J=1.6, 5.5 Hz), 9.00 (1H, d, J=4.7 Hz), 9.30 (1H, d, J=1.6 Hz)

MS: [M+H]$^+$=432
Melting point: 191° C. (de comp.)
Specific optical rotation; [α]$_D$=−53.71 (c=0.5, chloroform)
Chiral HPLC condition;
Column; DAICEL CHIRALCEL OD-H 250×4.60 mm
Eluent; ethanol/n-hexane=80/20
Flow rate; 0.5 ml/min
Temperature; 40° C.
Detection; 242 nm (UV)
Retention time; 23.878 min (ref. other isomer; 30.615 min)

Preparation of Comparative Compounds

Example 2

Preparation of Compound 1 of Table 1

1-Methyl-2-[2-(3-phenyl-[1,2,4]oxadiazol-5-yl)-morpholin-4-yl]-1H-[4,4']bipyrimidinyl-6-one

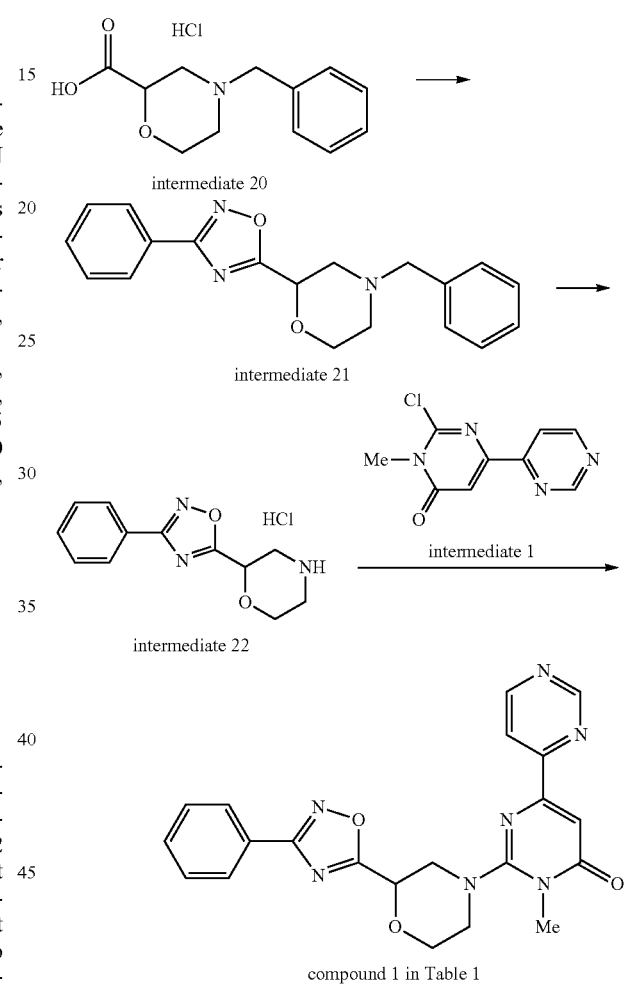

Step 2-1: 4-Benzyl-2-(3-phenyl-1,2,4-oxadiazol-5-yl)morpholine (intermediate 21)

To a stirred solution of 4-benzyl-2-morpholinecarboxylic acid hydrochloride (intermediate 20, 1.5 g, 5.82 mmol) in N,N-dimethylformamide (10 ml) was added 2-(1H-benzotriazole-1-yl)-1,1,3,3-tetramethyluroniumtetrafluoroborate (2.2 g, 6.98 mmol), 1-hydroxybenzotriazole hydrate (236 mg, 1.74 mmol) and N,N-diisopropylethylamine (5.1 ml, 29.1 mmol), and the reaction mixture was stirred at room temperature for 30 minutes. After the addition of N'-hydroxybenzamidine (792 mg, 5.82 mmol), the reaction mixture was stirred at room temperature for one hour, and then heated to 110° C. When the reaction was complete (checked by thin layer chromatography), excess reagent was decomposed by the addition of water and the aqueous layer was extracted with ethyl acetate. The extract was washed with water and brine, dried over magnesium sulfate, and concentrated in vacuo. The resulting residue was purified by column chromatography on silica gel, (eluent; 25% ethyl acetate in hexane) to afford 4-benzyl-2-(3-phenyl-1,2,4-oxadiazol-5-yl)morpholine (intermediate 21, 1.44 g, 77%) as a colorless oil.

$^1$H NMR (400 MHz, CDCl$_3$) δ: 2.41-2.47 (1H, m), 2.60 (1H, dd, J=9.8, 11.1 Hz), 2.73 (1H, dd, J=1.2, 11.7 Hz), 3.13 (1H, d, J=11.7 Hz), 3.61 (2H, s), 3.85-3.91 (1H, m), 4.11 (1H, dt, J=3.0, 11.5 Hz), 4.99 (1H, dd, J=2.8, 9.4 Hz), 7.26-7.38 (5H, m), 7.45-7.52 (3H, m), 8.09-8.12 (2H, m)

MS: [M+H]$^+$=322

Step 2-2: 2-(3-Phenyl-[1,2,4]oxadiazol-5-yl)-morpholine Hydrochloride (Intermediate 22)

To a stirred solution of 4-benzyl-2-(3-phenyl-1,2,4-oxadiazol-5-yl)morpholine (intermediate 21, 2.0 g, 6.22 mmol) in 1,2-dichloroethane (10 ml) was added chloroethyl chloroformate (2.0 ml, 18.7 mmol), and the reaction mixture was stirred for at 70° C. 4 hours. The reaction mixture was concentrated in vacuo. After removal of the solvent, the residue was dissolved in methanol (10 ml), and the reaction solution was stirred for one hour under reflux. When the reaction was complete (checked by thin layer chromatography), the reaction mixture was concentrated in vacuo. The resulting 2-(3-phenyl-[1,2,4]oxadiazol-5-yl)-morpholine hydrochloride (intermediate 22) was used for next reaction without further purification.

$^1$H NMR (400 MHz, DMSO-d$_6$) δ: 3.15-3.22 (1H, m), 3.29-3.32 (1H, m), 3.47 (1H, dd, J=10.2, 12.6 Hz), 3.72 (1H, dd, J=2.6, 12.8 Hz), 4.00-4.06 (1H, m), 4.12-4.17 (1H, m), 5.40 (1H, dd, J=2.8, 10.0 Hz), 7.58-7.66 (3H, m), 8.03-8.05 (2H, m), 9.65 (2H, br)

MS: [M+H]$^+$=232

Melting point: 194.1° C.

Step 2-3: 1-Methyl-2-(2-(3-phenyl-[1,2,4]oxadiazol-5-yl)-morpholin-4-yl)-1H-[4,4']bipyrimidinyl-6-one: (Compound 1 of Table 1)

A solution of 2-(3-phenyl-[1,2,4]oxadiazol-5-yl)-morpholine hydrochloride (intermediate 22) obtained above in tetrahydrofuran (10 ml) was added with 2-chloro-3-methyl-6-(pyrimidine-4-yl)pyrimidin-4-one (intermediate 1, 1.3 g, 6.22 mmol) and triethylamine (4.3 ml, 31.1 mmol), and the reaction mixture was stirred at room temperature for 2 hours. The solution was partitioned between water and chloroform, and the organic layer was washed with water and brine, dried over magnesium sulfate, and concentrated in vacuo. The resulting residue was purified by column chromatography on silica gel (eluent; 5% methanol in chloroform) to afford 1-methyl-2-(2-(3-phenyl-[1,2,4]oxadiazol-5-yl)-morpholin-4-yl)-1H-[4,4']bipyrimidinyl-6-one (compound 1 of Table 1, 1.53 g, 59%, 2 steps) as a solid.

$^1$H NMR (400 MHz, DMSO-d$_6$) δ: 3.47 (3H, s), 3.60-3.70 (3H, m), 3.89-4.11 (3H, m), 5.28-5.39 (1H, m), 7.02 (1H, s), 7.56-7.62 (3H, m), 8.00-8.02 (2H, m), 8.24 (1H, d, J=4.6 Hz), 9.00 (1H, d, J=4.6 Hz), 9.29 (1H, s).

MS: 418 (M$^+$+1).

Melting point: 166.7° C.

Example 3

Preparation of the Compound 2 in Table 1

1-Methyl-2-[2-(5-phenyl-[1,2,4]oxadiazol-3-yl)-morpholin-4-yl]-1H-[4,4']bipyrimidinyl-6-one

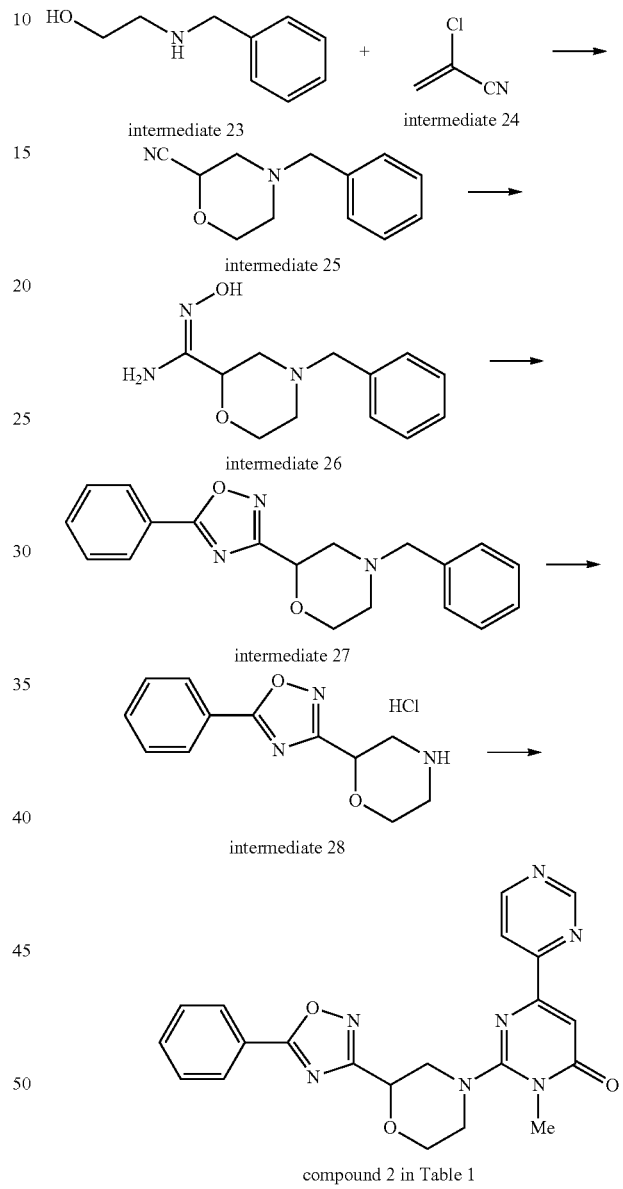

Step 3-1: 4-Benzylmorpholine-2-carbonitrile (Intermediate 25)

A mixture of N-benzylethanolamine (intermediate 23, 44.8 ml, 314 mmol) and 2-chloroacrylonitrile (intermediate 24, 25 ml, 314 mmol) was stirred at room temperature for 24 hours. After the mixture was cooled to 0° C., tetrahydrofuran (300 ml) and then potassium tert-butoxide was added to the mixture, and the mixture was stirred at 0° C. for one hour. The mixture was diluted by ethyl ether, and then washed with water and brine and dried over magnesium sulfate. Solvent was removed under reduced pressure, and the residue was purified by silica gel column chromatography (eluent; 5% ethyl acetate in hexane) to afford 4-benzylmorpholine-2-carbonitrile (intermediate 25) as colorless oil.

$^1$H NMR (400 MHz, CDCl$_3$) δ: 2.41 (1H, ddd, J=3.1, 8.8, 11.8 Hz), 2.56 (1H, dd, J=3.2, 11.9 Hz), 2.64 (1H, d, J=11.8 Hz), 2.76 (1H, dd, J=3.8, 11.8 Hz), 3.57 (2H, q, J=12.9 Hz), 3.77 (1H, dt, J=3.6, 11.7 Hz), 4.03 (1H, ddd, J=2.7, 8.9, 11.7 Hz), 4.60 (1H, t, J=3.6 Hz), 7.26-7.36 (5H, m)

MS: $[M+H]^+$=203

Step 3-2: 4-Benzyl-N'-hydroxymorpholine-2-carboxamidine (Intermediate 26)

To a stirred solution of 4-benzylmorpholine-2-carbonitrile (intermediate 25, 5.0 g, 24.7 mmol) in the mixture of ethanol and water (2/1, 75 ml) was added hydroxylamine hydrochloride (5.2 g, 74.2 mmol) and sodium bicarbonate (13.1 g, 123.5 mmol), and the reaction mixture was stirred under reflux for 12 hours. The reaction was diluted with chloroform, and the reaction mixture was washed with water and brine. The organic layer was dried over magnesium sulfate, and concentrated in vacuo. The resulting 4-benzyl-N'-hydroxymorpholine-2-carboxamidine (intermediate 26) was used for next reaction without further purification.

Step 3-3: 4-Benzyl-2-(5-phenyl-1,2,4-oxadiazol-3-yl)morpholine (Intermediate 27)

To a stirred solution of benzoic acid (2.30 g, 19.1 mmol) in N,N-dimethylformamide (20 ml) was added 2-(1H-benzotriazole-1-yl)-1,1,3,3-tetramethyluroniumtetrafluoroborate (6.15 g, 19.1 mmol), 1-hydroxybenzotriazole hydrate (518 mg, 3.83 mmol) and N,N-diisopropylethylamine (11.0 ml, 63.8 mmol), and the reaction mixture was stirred at room temperature for 30 minutes. After addition of 4-benzyl-N'-hydroxymorpholine-2-carboxamidine (intermediate 26, 3.0 g, 12.8 mmol), the reaction mixture was stirred at room temperature for one hour, and then heated to 110° C. When the reaction was complete (checked by thin layer chromatography), excess reagent was decomposed by addition of water and the aqueous layer was extracted with ethyl acetate. The extract was washed with water and brine, dried over magnesium sulfate, and concentrated in vacuo. The resulting residue was purified by column chromatography on silica gel (eluent: 30% ethyl acetate in hexane) to afford 4-benzyl-2-(5-phenyl-1,2,4-oxadiazol-3-yl)morpholine (intermediate 27, 3.08 g, 75%) as a colorless oil.

$^1$H NMR (400 MHz, CDCl$_3$) δ: 2.42 (1H, dt, J=3.3, 11.4 Hz), 2.54 (1H, dd, J=10.7 Hz), 2.76 (1H, dd, J=1.7, 11.5 Hz), 3.13 (1H, dd, J=2.0, 9.6 Hz), 3.61 (2H, s), 3.89 (1H, dt, J=2.5, 11.2 Hz), 4.07-4.11 (1H, m), 4.90 (1H, dd, J=2.5, 10.2 Hz), 7.26-7.36 (5H, m), 7.50-7.53 (2H, m), 7.57-7.61 (1H, m), 8.15-8.16 (2H, m)

MS: $[M+H]^+$=322

Step 3-4: 2-(5-Phenyl-[1,2,4]oxadiazol-3-yl)-morpholine Hydrochloride (Intermediate 28)

To a stirred solution of 4-benzyl-2-(5-phenyl-1,2,4-oxadiazol-3-yl)morpholine (intermediate 27, 900 mg, 2.80 mmol) in 1,2-dichloroethane (2.0 ml) was added chloroethyl chloroformate (0.46 ml, 4.20 mmol), and the reaction mixture was stirred at 70° C. for 4 hours. The reaction mixture was concentrated in vacuo. After removal of the solvent, the residue was dissolved in methanol (2.0 ml), and the solution was stirred under reflux for one hour. When the reaction was complete (checked by thin layer chromatography), the reaction mixture was concentrated in vacuo. The resulting 2-(5-phenyl-[1,2,4]oxadiazol-3-yl)-morpholine hydrochloride (intermediate 28) was used for next reaction without further purification.

$^1$H NMR (400 MHz, DMSO-d$_6$) δ: 3.17-3.24 (1H, m), 3.30-3.44 (2H, m), 3.60-3.64 (1H, m), 3.99 (1H, dt, J=2.3, 12.0 Hz), 4.11-4.15 (1H, m), 5.16 (1H, dd. J=2.6, 10.7 Hz), 7.66 (2H, t, J=7.7 Hz), 7.73-7.77 (1H, m), 8.12-8.15 (2H, m), 9.42 (2H, br)

MS: $[M+H]^+$=232

Melting point: 111.0° C.

Step 3-5: 1-Methyl-2-[2-(5-phenyl-[1,2,4]oxadiazol-3-yl)-morpholin-4-yl]-1H-[4,4']bipyrimidinyl-6-one (Compound 2 in Table 1)

A solution of the resulting 2-(5-phenyl-[1,2,4]oxadiazol-3-yl)-morpholine hydrochloride (intermediate 10 in tetrahydrofuran (6.0 ml) was added with 2-chloro-3-methyl-6-(pyrimidine-4-yl)pyrimidin-4-one (intermediate 1, 260 mg, 2.34 mmol) and triethylamine (1.81 ml, 13.0 mmol), and the reaction mixture was stirred at room temperature for 2 hours. The solution was partitioned between water and chloroform, and the organic layer was washed with water and brine, dried over magnesium sulfate, and concentrated in vacuo. The resulting residue was purified by column chromatography on silica gel (eluent; 5% methanol in chloroform) to afford 1-methyl-2-[2-(5-phenyl-[1,2,4]oxadiazol-3-yl)-morpholin-4-yl]-1H-[4, 4']bipyrimidinyl-6-one (compound 2 in Table 1, 749 mg, 64%, 2 steps) as solid $^1$H NMR (400 MHz, DMSO-d$_6$) δ: 3.47 (3H, s), 3.51-3.68 (3H, m), 3.96-4.10 (3H, m), 5.15-5.17 (1H, m), 7.02 (1H, s), 7.67-7.74 (3H, m), 8.13-8.24 (3H, m), 9.00 (1H, d, J=4.8 Hz), 9.30 (1H, s).

MS: 418 ($M^+$+1).

Melting point: 207.6° C.

Example 4

Preparation of the Compound 3 in Table 1

2-[2-(4-Furan-3-yl-phenyl)-morpholin-4-yl]-1-methyl-1H-[4,4']bipyrimidinyl-6-one

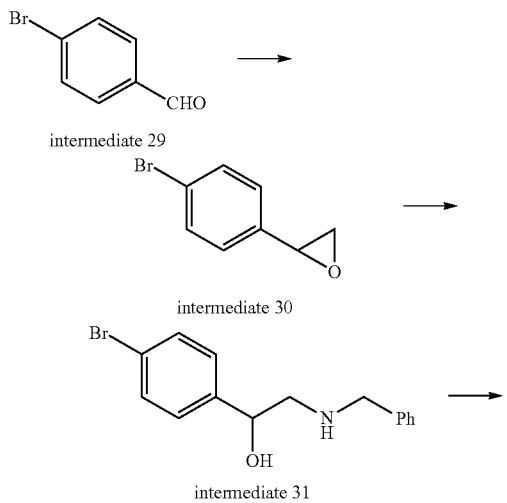

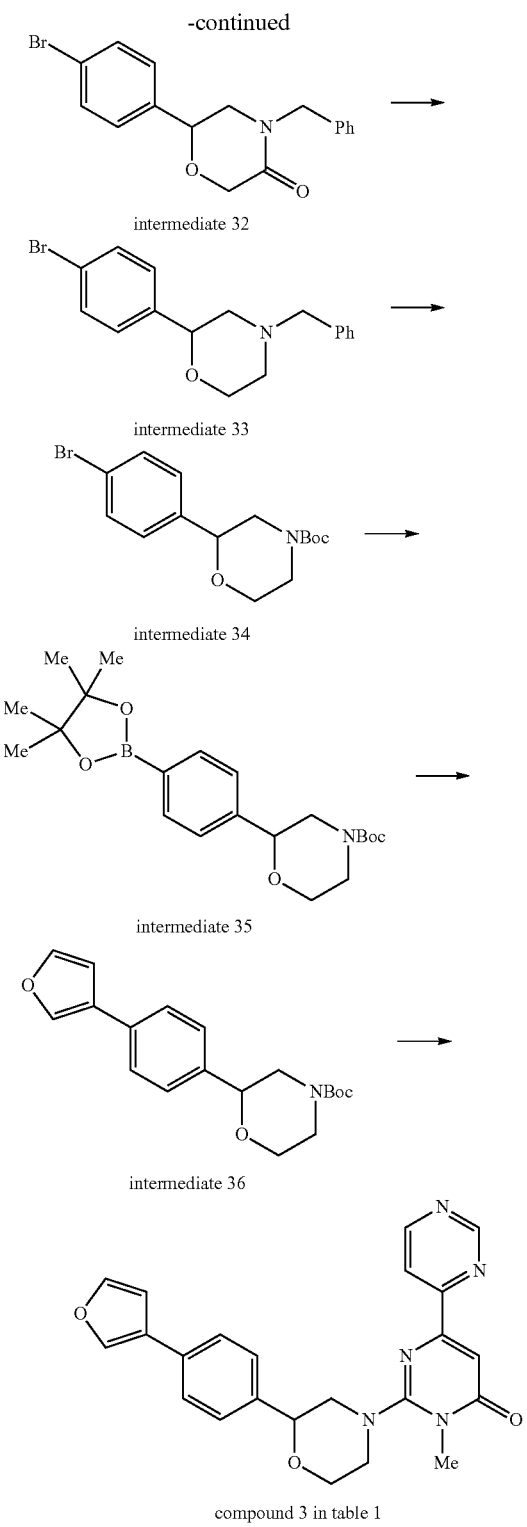

intermediate 32 intermediate 33 intermediate 34 intermediate 35 intermediate 36 compound 3 in table 1

Step 4-1: 2-(4-Bromophenyl)oxirane (Intermediate 30)

A mixture of 4-bromobenzaldehyde (intermediate 29, 25.25 g, 136 mmol), trimethylsulfonium iodide (28.71 g, 141 mmol), water (6.5 ml, 361 mmol) and potassium hydroxide (15.56 g, 277 mmol) in acetonitrile (140 ml) was warmed to 55° C. for 2.5 hours. The resulting solution was partitioned between water and diethyl ether, and the organic layer was washed with water, diluted hydrochloric acid, and brine, and dried over sodium sulfate. Crude product of 2-(4-bromo-phenyl)-oxirane (intermediate 30) was obtained by removal of organic solvent under reduced pressure, which was used for next reaction without purification.

Step 4-2: 2-Benzylamino-1-(4-bromo-phenyl)-ethanol (Intermediate 31)

A mixture of crude product of 2-(4-bromo-phenyl)-oxirane (intermediate 30) obtained above and benzylamine (47.00 g, 439 mmol) was heated to 70° C. for 8 hours and the excess benzylamine was distilled off under reduced pressure (ca. 65° C. at 10 mmHg). The residue was cooled to be solidified, which was washed with diisopropyl ether to afford 2-benzylamino-1-(4-bromo-phenyl)-ethanol (intermediate 31, 23.63 g, 57% from 4-bromobenzaldehyde) as a white solid.

$^1$H NMR (400 MHz, CDCl$_3$) δ: 2.68 (1H, dd, J=9.0, 12.2 Hz), 2.92 (1H, dd, J=3.6, 12.2 Hz), 3.79-3.87 (2H, m), 4.67 (1H, dd, J=3.6, 8.9 Hz), 7.22-7.36 (7H, m), 7.44-7.47 (2H, m)

MS: [M+H]$^+$=306

Melting point: 108.8° C.

Step 4-3: 4-Benzyl-6-(4-bromo-phenyl)-morpholin-3-one (Intermediate 32)

After addition of chloroacetyl chloride (8.49 g, 75.2 mmol) in toluene (30 ml) to a ice-cooled solution of 2-benzylamino-1-(4-bromo-phenyl)-ethanol (intermediate 31, 21.85 g, 71.4 mmol) in toluene (300 ml), a solution of triethylamine (10.25 g, 101 mmol) in toluene (20 ml) was added to the mixture and stirred for one hour. Sodium methoxide (28% solution in methanol, 45.73 g, 237 mmol) in methanol (30 ml) was then added to the solution and stirred for 2 hours. Reaction was quenched by adding dilute hydrochloric acid to adjust the pH around 7.0, and partitioned between water and ethyl acetate. The organic layer was washed with dilute hydrochloric acid, water, saturated aqueous sodium bicarbonate, and brine and dried over sodium sulfate. Solvents were removed under reduced pressure, and the residue was purified by silica gel column chromatography (eluent; hexane/ethyl acetate=1/1) to afford 4-benzyl-6-(4-bromo-phenyl)-morpholin-3-one (intermediate 32, 21.26 g, 86%) as a colorless oil.

$^1$H NMR (400 MHz, CDCl$_3$) δ: 3.26 (1H, dd, J=3.4, 12.3 Hz), 3.35 (1H, dd, J=10.4, 12.3 Hz), 4.47 (1H, d, J=16.8 Hz), 4.51 (1H, d, J=16.6 Hz), 4.56 (1H, d, J=14.6 Hz), 4.72 (1H, d, J=14.8 Hz), 7.19 (2H, d, J=8.4 Hz), 7.27-7.38 (5H, m), 7.47 (2H, d, J=8.5 Hz)

MS: [M+H]$^+$=346

Step 4-4: 4-Benzyl-2-(4-bromo-phenyl)-morpholine (Intermediate 33)

To a solution of 4-benzyl-6-(4-bromo-phenyl)-morpholin-3-one (intermediate 32, 18.70 g, 54 mmol) in tetrahydrofuran (100 ml) was added a solution of borane-tetrahydrofuran complex in tetrahydrofuran (0.9 M, 170 ml, 153 mmol) dropwise at 0° C. under nitrogen atmosphere. The resulting mixture was warmed to room temperature and stirred for 3 hours. After cooling to 0° C., the reaction was quenched by the slow addition of methanol (30 ml). The clear mixture was evaporated under reduced pressure and the residual oil was diluted with 1N aqueous sodium hydroxide (300 ml). The resulting aqueous mixture was stirred at 100° C. for 3 hours and cooled to room temperature. The afforded organic materials were extracted with ethyl acetate and the combined extracts were dried over anhydrous sodium sulfate. After concentration, the residue was purified by silica gel column chromatography (eluent; hexane/ethyl acetate=3/1) to yield 4-benzyl-2-(4-bromo-phenyl)-morpholine (intermediate 33, 17.30 g, 52 mmol, 96%) as colorless oil. $^1$H NMR (400 MHz, CDCl$_3$) δ: 2.26 (1H, dt, J=3.4, 11.5 Hz), 2.74 (1H, dd, J=1.6, 11.5 Hz), 2.85-2.89 (1H, m), 3.82 (1H, dt, J=2.5, 11.4 Hz), 3.98-4.02 (1H, m), 4.53 (1H, d, J=2.2, 10.2 Hz), 7.21 (2H, d, J=8.3 Hz), 7.45 (2H, d, J=8.2 Hz)

MS: [M+H]$^+$=332

Step 4-5: 2-(4-Bromo-phenyl)-morpholine-4-carboxylic Acid Tert-butyl Ester (Intermediate 34)

To a solution of 4-benzyl-2-(4-bromo-phenyl)-morpholine (intermediate 33, 10.0 g, 30 mmol) in dichloroethane (90 ml) was added chloroethyl chloroformate (4.0 ml, 36 mmol) at room temperature and the resulting solution was refluxed for one hour. After cooling to room temperature, the mixture was concentrated under reduced pressure. The residue was diluted with methanol (100 ml) and the resulting solution was refluxed for one hour. Methanol was evaporated and ethyl acetate was added to the residual solid. After triturating, white solid was collected by filtration and dried under reduced pressure. The obtained solid was suspended with tetrahydrofuran (60 ml) and to the resulting mixture was added di-tert-butyl dicarbonate (6.50 g, 30 mmol) and 1N aqueous sodium hydroxide (60 ml, 60 mmol) at room temperature. After 2 hours stirring, extractive workup with ethyl acetate was performed and the combined organic phase was dried over anhydrous sodium sulfate followed by concentration. The resulting solid was washed with hexane to afford 2-(4-bromo-phenyl)-morpholine-4-carboxylic acid tert-butyl ester (intermediate 34, 9.08 g, 26.5 mmol, 88%) as a white solid, which was used for next reaction without further purification $^1$H NMR (400 MHz, CDCl$_3$) δ: 1.48 (9H, s), 2.77 (2H, br), 3.03 (1H, br), 3.67 (1H, dt, J=2.4, 11.7 Hz), 3.94 (2H, br), 4.01 (1H, d, J=10.8 Hz), 4.37 (1H, d, J=10.2 Hz), 7.24-7.26 (2H, m), 7.48-7.50 (2H, m)

MS: [M+H]$^+$=242 (-tert-butoxycarbonyl)

Melting point: 97.5° C.

Step 4-6: 2-[4-(4,4,5,5-Tetramethyl-[1, 3,2]dioxaborolan-2-yl)-phenyl]-morpholine-4-carboxylic Acid Tert-butyl Ester (Intermediate 35)

A mixture of 2-(4-bromo-phenyl)-morpholine-4-carboxylic acid tert-butyl ester (intermediate 34, 6 g, 17.5 mmol), bis(pinacolato)diboron (5.1 g, 20 mmol), potassium acetate (3.5 g, 36 mmol) and [1,1'-bis(diphenylphosphino)ferrocene]dichloropalladium(II) (1.2 g, 1.5 mmol) in N,N-dimethylformamide (40 ml) was heated to 80° C. under nitrogen atmosphere. After stirring for 3 hours, the reaction mixture was cooled to room temperature and poured into water. Extractive workup was performed with ethyl acetate and the organic phase was washed with brine. The collected organic layer was dried over sodium sulfate and concentrated. The resulting material was purified by flash column chromatography on silica gel (hexane/ethyl acetate=5/1 as an eluent). 2-[4-(4,4,5,5-tetramethyl-[1,3,2]dioxaborolan-2-yl)-phenyl]-morpholine-4-carboxylic acid tert-butyl ester (intermediate 35, 5.6 g, 14.5 mmol, 83% yield) was obtained as a white solid.

$^1$H NMR (400 MHz, CDCl$_3$) δ: 1.34 (12H, s), 1.48 (9H, s), 2.80 (1H, br), 3.05 (1H, br), 3.68 (1H, dt, J=2.3, 11.7 Hz), 3.94 (2H, br), 4.03 (1H, d, J=10.4 Hz), 4.43 (1H, d, J=9.8 Hz), 7.38 (2H, d, J=7.9 Hz), 7.81 (2H, d, J=7.9 Hz)

MS: [M+H]$^+$=290 (-tert-butoxycarbonyl)

Melting point: 129.4° C.

Step 4-7: 2-(4-Furan-3-yl-phenyl)-morpholine-4-carboxylic Acid Tert-Butyl Ester (Intermediate 36)

A mixture of 2-[4-(4,4,5,5-tetramethyl-[1,3,2]dioxaborolan-2-yl)-phenyl]-morpholine-4-carboxylic acid tert-butyl ester (1.0 g, 2.6 mmol), 3-bromofuran (0.27 ml, 3.0 mmol), tetrakis(triphenylphosphine)palladium(0) (0.35 g, 0.3 mmol) and 2N aqueous potassium carbonate solution (4.5 ml) in N,N-dimethylformamide (5 ml) was heated to 80° C. under nitrogen atmosphere and stirred for 3 hours. The reaction mixture was poured into water and extracted with ethyl acetate. The organic phase was washed with brine and dried over sodium sulfate. After concentration, the residue was purified to afford 2-(4-furan-3-yl-phenyl)-morpholine-4-carboxylic acid tert-butyl ester (intermediate 36, 0.73 g, 2.2 mmol, 85% yield) as a white solid by silica gel column chromatography (eluent; hexane/ethyl acetate=3/1).

$^1$H NMR (400 MHz, CDCl$_3$) δ: 1.49 (9H, s), 2.85 (1H, br), 3.06 (1H, br), 3.69 (1H, dt, J=2.6, 11.8 Hz), 3.96 (2H, br), 4.03 (1H, d, J=10.1 Hz), 4.43 (1H, d, J=9.2 Hz), 6.70 (1H, d, J=1.3 Hz), 7.38 (2H, d, J=8.0 Hz), 7.47-7.49 (3H, m), 7.73 (1H, s)

MS: [M+H]$^+$=230 (-tert-butoxycarbonyl)

Melting point: 114.0° C.

Step 4-8: 2-[2-(4-Furan-3-yl-phenyl)-morpholin-4-yl]-1-methyl-1H-[4,4']bipyrimidinyl-6-one (Compound 3 in Table 1)

2-(4-Furan-3-yl-phenyl)-morpholine-4-carboxylic acid tert-butyl ester (intermediate 36, 0.73 g, 2.2 mmol) was dissolved in 4N hydrogen chloride in ethyl acetate solution at room temperature and the mixture was stirred for 2 hours. After concentration of the reaction mixture, the resulting solid materials were collected. The obtained solid was suspended with tetrahydrofuran (10 ml). To the mixture was added 2-chloro-3-methyl-6-(pyrimidin-4-yl)-3H-pyrimidin-4-one (intermediate 1, 0.33 g, 1.5 mmol) and triethylamine (0.62 ml, 4.5 mmol) at room temperature. After stirring for 6 hours, the resulting mixture was poured into water and extracted with chloroform. The organic solution was dried over sodium sulfate and concentrated. The residue was purified by flash column chromatography on silica gel (chloroform/methanol=95/5 as an eluent) to yield 2-[2-(4-furan-3-yl-phenyl)-morpholin-4-yl]-1-methyl-1H-[4,4']bipyrimidinyl-6-one (compound 3 in Table 1, 0.55 g, 1.3 mmol, 87%) as a white solid.

$^1$H NMR (400 MHz, DMSO-d$_6$) δ: 3.04 (1H, dd, J=10.8, 12.8 Hz), 3.20 (1H, dt, J=2.8, 12.4 Hz), 3.49 (3H, s), 3.71 (1H, d, J=13.4 Hz), 3.76 (1H, d, J=12.9 Hz), 3.92 (1H, dt, J=1.8, 11.7 Hz), 4.10 (1H, dd, J=1.8, 11.6 Hz), 4.76 (1H, dd, J=1.9, 10.6 Hz), 6.98 (1H, s), 7.02 (1H, s), 7.47 (1H, d, 8.2 Hz), 7.64

(1H, d, J=8.3 Hz), 7.75 (1H, d, J=1.6 Hz), 8.21-8.22 (2H, m), 8.99 (1H, d, J=5.1 Hz), 9.30 (1H, s)

MS: [M+H]$^+$=416

Melting point: 219.4° C. (decomp.)

Example 5

Preparation of the Compound 4 in Table 1

1-Methyl-2-{2-[4-(1-methyl-1H-imidazol-2-yl)-phenyl]-morpholin-4-yl}-1H-[4,4']bipyrimidinyl-6-one

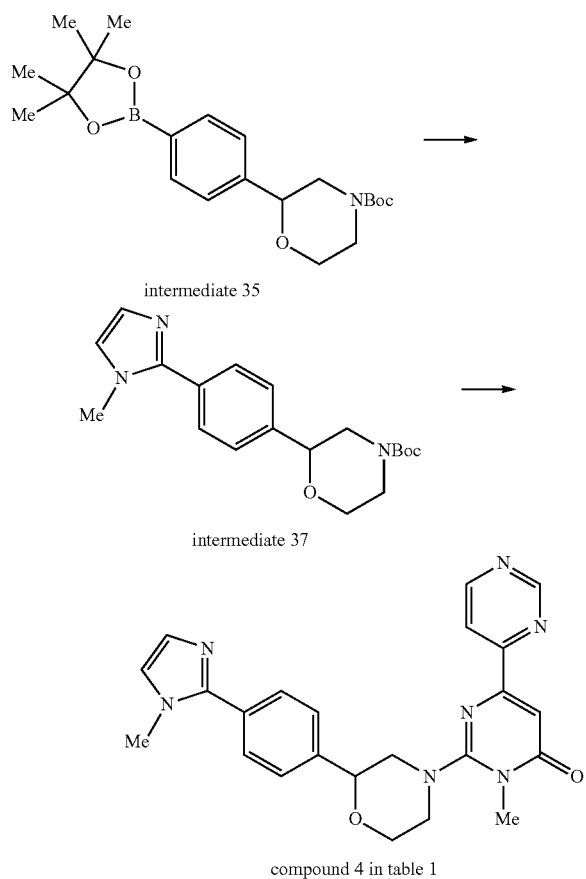

Step 5-1; 2-[4-(1-Methyl-1H-imidazol-2-yl)-phenyl]-morpholine-4-carboxylic Acid Tert-butyl Ester (Intermediate 37)

A mixture of 2-[4-(4,4,5,5-tetramethyl-[1,3,2]dioxaborolan-2-yl)-phenyl]-morpholine-4-carboxylic acid tert-butyl ester (intermediate 35, 1.0 g, 2.6 mmol), 2-bromo-1-methyl imidazole (0.29 mL, 3.0 mmol), tetrakis(triphenylphosphine)palladium(0) (0.35 g, 0.3 mmol) and 2N aqueous potassium carbonate (4.5 ml) in N,N-dimethylformamide (5 ml) was heated to 80° C. under nitrogen atmosphere and stirred for 3 hours. The reaction mixture was poured into water and extracted with ethyl acetate. The organic phase was washed with brine and dried over sodium sulfate. After concentration, the residue was purified by silica gel column chromatography (eluent; ethyl acetate) to afford 2-[4-(1-methyl-1H-imidazol-2-yl)-phenyl]-morpholine-4-carboxylic acid tert-butyl ester (intermediate 37, 0.40 g, 1.2 mmol, 45%) as colorless oil.

$^1$H NMR (400 MHz, CDCl$_3$) δ: 1.49 (9H, s), 2.85 (1H, br), 3.07 (1H, br), 3.66-3.76 (1H, m), 3.75 (3H, s), 3.95 (2H, br), 4.05 (1H, d, J=9.8 Hz), 4.47 (1H, d, J=9.1 Hz), 6.97 (1H, s), 7.12 (1H, d, J=1.0 Hz), 7.47 (2H, d, J=8.1 Hz), 7.64 (2H, d, J=8.3 Hz)

MS: [M+H]$^+$=344

Step 5-2: 1-Methyl-2-{2-[4-(1-methyl-1H-imidazol-2-yl)-phenyl]-morpholin-4-yl}-1H-[4,4']bipyrimidinyl-6-one (Compound 4 in Table 1)

2-[4-(1-Methyl-1H-imidazol-2-yl)-phenyl]-morpholine-4-carboxylic acid tert-butyl ester (intermediate 37, 0.40 g, 1.2 mmol) was dissolved in 4N hydrogen chloride in ethyl acetate (5 ml) at room temperature and the mixture was stirred for 2 hours. After concentration of the reaction mixture, the resulting solid materials were collected. The obtained solid was suspended with tetrahydrofuran (10 ml). To the mixture was added 2-chloro-3-methyl-6-(pyrimidin-4-yl)-3H-pyrimidin-4-one (intermediate 1, 0.18 g, 0.8 mmol) and triethylamine (0.42 ml, 3 mmol) at room temperature. After stirring for 6 hours, the resulting mixture was poured into water and extracted with chloroform. The organic solution was dried over sodium sulfate and concentrated. The residue was purified by silica gel column chromatography (eluent; chloroform/methanol=95/5) to yield 1-methyl-2-{2-[4-(1-methyl-1H-imidazol-2-yl)-phenyl]-morpholin-4-yl}-1H-[4,4']bipyrimidinyl-6-one (compound 4 in Table 1, 0.12 g, 0.3 mmol, 35%) as a white solid.

$^1$H NMR (400 MHz, DMSO-d$_6$) δ: 3.07 (1H, dd, J=10.8, 12.8 Hz), 3.18-3.26 (1H, m), 3.50 (3H, s), 3.73 (1H, d, J=13.1 Hz), 3.76 (3H, s), 3.82 (1H, d, J=13.0 Hz), 3.94 (1H, dt, J=2.1, 11.7 Hz), 4.10 (1H, d, J=13.1 Hz), 4.82 (1H, dd, J=1.9, 10.3 Hz), 6.98 (1H, s), 7.02 (1H, s), 7.26 (1H, s), 7.57 (2H, d, J=8.3 Hz), 7.71 (2H, d, J=8.4 Hz), 8.23 (1H, dd, J=1.2, 5.4 Hz), 9.00 (1H, d, J=5.0 Hz), 9.30 (1H, d, J=1.1 Hz)

MS: [M+H]$^+$=430

Melting point: 179.8° C. (decomp.)

Example 6

Preparation of the Compound 5 in Table 1

1-Methyl-2-[2-(4-pyrazol-1-yl-phenyl)-morpholin-4-yl]-1H-[4,4']bipyrimidinyl-6-one

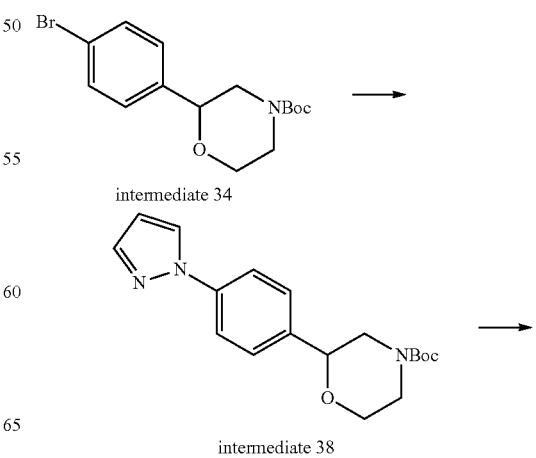

-continued

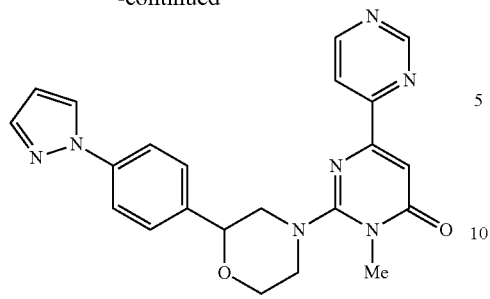

compound 5 in table 1

Step 6-1: 2-(4-Pyrazol-1-yl-phenyl)-morpholine-4-carboxylic Acid Tert-butyl Ester (Intermediate 38)

A mixture of 2-(4-bromo-phenyl)-morpholine-4-carboxylic acid tert-butyl ester (intermediate 34, 3.0 g, 8.8 mmol), copper (I) iodode (0.05 g, 0.3 mmol), sodium iodide (1.8 g, 12 mmol) and trans-N,N'-dimethylcyclohexane-1,2-diamine (0.1 ml, 0.6 mmol) in toluene (10 ml) was refluxed under nitrogen atmosphere for 3 hours. After the mixture was cooled to room temperature, pyrazole (0.68 g, 10 mmol) and potassium phosphate (6.4 g, 30 mmol) was added to the mixture. The resulting mixture was refluxed for 3 hours and then cooled to room temperature. After removal of solid materials by filtration, the filtrate was poured into water and extracted with ethyl acetate. The organic layer was dried over sodium sulfate and concentrated. The residue was purified by flash column chromatography on silica gel to give 2-(4-pyrazol-1-yl-phenyl)-morpholine-4-carboxylic acid tert-butyl ester (intermediate 38, 1.7 g, 5.3 mmol, 60%) as a white solid.

$^1$H NMR (400 MHz, CDCl$_3$) δ: 1.49 (9H, s), 2.84 (1H, br), 3.06 (1H, br), 3.70 (1H, dt, J=2.4, 11.7 Hz), 4.04 (1H, d, J=10.1 Hz), 4.46 (1H, d, J=8.8 Hz), 6.47 (1H, t, J=2.0 Hz), 7.47 (2H, d, J=8.6 Hz), 7.70 (2H, d, J=8.5 Hz), 7.72 (1H, d, J=1.3 Hz), 7.93 (1H, d, J=2.4 Hz)

MS: [M+H]$^+$=230 (-tert-butoxycarbonyl)

Melting point: 87.3° C.

Step 6-2: 1-Methyl-2-[2-(4-pyrazol-1-yl-phenyl)-morpholin-4-yl]-1H-[4,4']bipyrimidinyl-6-one (Compound 5 in Table 1)

2-(4-Pyrazol-1-yl-phenyl)-morpholine-4-carboxylic acid tert-butyl ester (intermediate 38, 1.74 g, 5.3 mmol) was dissolved in 4N hydrogen chloride in ethyl acetate (10 ml) at room temperature and the mixture was stirred for 2 hours. After concentration of the reaction mixture, the resulting solid materials were collected. The part of obtained solid (500 mg) was suspended with tetrahydrofuran (20 ml). To the mixture was added 2-chloro-3-methyl-6-(pyrimidin-4-yl)-3H-pyrimidin-4-one (intermediate 1, 0.33 g, 1.5 mmol) and triethylamine (0.62 ml, 4.5 mmol) at room temperature. After stirring for 6 hours, the resulting mixture was poured into water and extracted with chloroform. The organic solution was dried over sodium sulfate and concentrated. The residue was purified by silica gel column chromatography (eluent; chloroform/methanol=95/5) to yield 1-methyl-2-[2-(4-pyrazol-1-yl-phenyl)-morpholin-4-yl]-1H-[4,4']bipyrimidinyl-6-one (compound 5 in Table 1, 0.44 g, 1.0 mmol, 70%) as a white solid.

$^1$H NMR (400 MHz, DMSO-d$_6$) δ: 3.05 (1H, dd, J=10.7, 12.8 Hz), 3.21 (1H, dt, J=2.5, 12.5 Hz), 3.49 (3H, s), 3.72 (1H, d, J=13.0 Hz), 3.79 (1H, d, J=13.0 Hz), 3.94 (1H, dt, J=1.8, 11.6 Hz), 4.10 (1H, dd, J=1.9, 11.7 Hz), 4.80 (1H, dd, J=1.8, 10.4 Hz), 6.56 (1H, t, J=2.0 Hz), 7.02 (1H, s), 7.59 (2H, d, J=8.6 Hz), 7.76 (1H, d, J=1.4 Hz), 7.87 (2H, d, 8.6 Hz), 8.22 (1H, dd, J=1.1, 5.3 Hz), 8.52 (1H, d, J=2.5 Hz), 9.00 (1H, d, J=5.2 Hz), 9.30 (1H, d, J=1.2 Hz)

MS: [M+H]$^+$=416

Melting point: 183.5° C.

Biological Assays

Experiment 7

Inhibitory Activity on Tau Phosphorylation In Vivo

Test compound was administered to male CD-1 mice of 5-6 weeks weighing 25-35 g (Charles River Japan, inc.) at 10 mg/kg p.o. (0.5% polyethylen glycol sorbitan monolaurate 80 (Tween80)/water suspension) and after 1 h, mice were decapitated and cortex was promptly removed, followed by being frozen in liquid N$_2$. Cortex was directly homogenized with 2.3% sodium dodecyl sulfate (SDS) homogenization buffer (62.5 mM 2-amino-2-(hydroxymethyl)-1,3-propanediol hydrochloride (Tris-HCl), 2.3% SDS, 1 mM each of ethylendiaminetetraacetic acid (EDTA), ethylene glycol-bis(2-aminoethylether)-N,N,N',N'-tetraacetic acid (EGTA) and dithiothreitol (DTT), protease inhibitor cocktail (sigma P2714) containing 0.2 μM 4-(2-aminoethyl)benzenesulfonyl fluoride (AEBSF), 13 μM bestatin, 1.4 μM E-64, 0.1 mM leupeptin, 30 nM aprotinin, pH 6.8) and centrifuged at 15000×g for 15 min at 4° C. Protein concentrations were determined using DC protein assay kit (BIO-RAD). Supernatants were diluted with sample buffer (62.5 mM Tris-HCl, 25% glycerol, 2% SDS, 0.01% Bromophenol Blue, pH6.8) to adjust the protein concentrations around 0.5-2 mg/mg and then boiled for 5 min. Samples (10 μg) were separated on 10% sodium dodecyl sulfate-polyacrylamide electrophoresis (SDS-PAGE) mini slab gels and transferred onto polyvinylidene difluoride (PVDF) membranes. Membranes were incubated with phosphate buffered saline (PBS) containing 5% non-fat milk for 1 h at room temperature and then probed with pS396 anti-body (BIOSOURCE) over night at 4° C. Anti-rabbit IgG horseradish peroxidase (HRP) conjugated anti-body (Promega) was used as secondary anti-body. Membranes were visualized by Enhanced ChemiLuminescence (ECL) kit (Amersham Bioscience) and detected by LAS1000 (Fuji Photo Film).

TABLE 1

| COMPOUNDS | in vivo[1) ] 10 mg/kg |
|---|---|
| Compound of the present invention | 58.14** |
| 1 | 92.12 |
| 2 | 79.21 |
| 3 | 71.44 |
| 4 | 71.21 |
| 5 | 53.35** |

[1)] % phosphorylation against vehicle.
**data means statistically significant

Experiment 8

Inhibitory Activity on CYP2D6

The purpose of this pharmacokinetic study was to investigate the inhibitory effects of test compounds on the specific metabolic activity of human CYP isozymes using human recombinant CYPs in vitro. The test compounds at concentrations of 0.4, 2, 10 and 50 µmol/L (If test compounds show low solubility in DMSO, the concentration was set 0.2, 1, 5 and 25 µmol/L) or positive control was added to the reaction mixture containing CYP2D6. The specific substrate and positive control is ethylene glycol ester of luciferin-6'-methyl ether and quinidine, respectively. The substrate for the CYP isozyme was incubated with human recombinant CYPs in the presence or absence of the test compounds and the metabolic activity of the CYP isozyme was determined. The reaction mixture was preincubated at 37° C. without NADPH generating system. The reaction was started by the addition of NADPH generating system, and then terminated by the addition of acetonitrile. The activities of the human CYP isozymes were measured by fluorescence signal (CYP2D6) of reaction mixture. $IC_{50}$ value for each compound was calculated by setting the data of reaction mixture without compound as 100% activity.

TABLE 2

| COMPOUNDS | CYP 2D6 inhibition (µM)[1]) |
|---|---|
| Compound of the present invention | >50.0 |
| 1 | >50.0 |
| 2 | >25.0 |
| 3 | 2.3 |
| 4 | >50.0 |
| 5 | 1.9 |

[1])$IC_{50}$ value

Experiment 9

Procognitive Effect

Procognitive properties of the glycogen-synthase inhibitor, 3-methyl-2-((2S)-2-(4-(5-methyl-1,2,4-oxadiazol-3-yl)phenyl)morpholino)-6-(pyrimidin-4-yl)pyrimidin-4(3H)-one, have been characterized on episodic memory deficits in normal and scopolamine-treated mice. Episodic memory was evaluated in the object recognition (OR) test.

The object recognition task was performed in a dimly illuminated (30 Lux), Plexiglas open-field box. The objects to be discriminated were a black plastic sphere and a black plastic cap. Mice were submitted to a 10-min acquisition trial (first trial) during which they were individually placed in the open field in the presence of object A (sphere or cap). The mouse behaviour was registered on a videotape using a camera and the time the animal took to explore object A (when the animal's snout was directed toward the object at a distance #1 cm) were recorded. A 10-min retention trial (second trial) occurred 3 hr or 24 hr later. During this trial, object A and another object B were placed in the open field, and the times (tA and tB) the animal took to explore the two objects were recorded. A recognition index (RI) was defined as (tB/(tA+tB))×100. An absence of recognition is chance with a theorical value of 50%.

The deficit of memory was induced either by a 24 h delay between the acquisition and the retention trials, or by the administration of the muscarinic receptor antagonist scopolamine before the acquisition trial.

In normal mice, the inter-trial-interval between acquisition and retention sessions was 24 h, and 3-Methyl-2-((2S)-2-(4-(5-methyl-1,2,4-oxadiazol-3-yl)phenyl)morpholino)-6-(pyrimidin-4-yl)pyrimidin-4-(3H)-one was administered per os either twice, 1 h before each session, or once immediately after the acquisition session. In scopolamine-treated mice, the inter-trial-interval between acquisition and retention sessions was 3 h, scopolamine (1 mg/kg) was administered intraperitoneally 30 minutes before the acquisition session, and 3-methyl-2-((2S)-2-(4-(5-methyl-1,2,4-oxadiazol-3-yl)phenyl)morpholino)-6-(pyrimidin-4-yl)pyrimidin-4(3H)-one was administered per os 1 h before the acquisition session.

In normal mice, 3-methyl-2-((2S)-2-(4-(5-methyl-1,2,4-oxadiazol-3-yl) phenyl)morpholino)-6-(pyrimidin-4-yl)pyrimidin-4(3H)-one (1-3-10-30 mg/kg p.o.) increased significantly memory performance from the dose of 10 mg/kg, when administered orally 1 h before acquisition and retention sessions, indicating that treated mice remember the object explored 24 h before. RI values were 50%, 50.3%, 52.6%, 60.4%, and 62.9%, at 0, 1, 3, 10, 30 mg/kg, respectively.

To distinguish the effect on memory acquisition from that on memory consolidation, 3-methyl-2-((2S)-2-(4-(5-methyl-1,2,4-oxadiazol-3-yl)phenyl)morpholino)-6-(pyrimidin-4-yl)pyrimidin-4(3H)-one was administered once (3-10-30 mg/kg po) immediately after the acquisition phase.

3-Methyl-2-((2S)-2-(4-(5-methyl-1,2,4-oxadiazol-3-yl) phenyl)morpholino)-6-(pyrimidin-4-yl)pyrimidin-4(3H)-one ameliorated significantly object recognition at doses of 10 and 30 mg/kg, suggesting that the compound consolidates episodic memory at a minimal effective dose of 10 mg/kg. RI values were 50.7%, 54.6%, 58.6%, and 60.0%, at 0, 3, 10, 30 mg/kg, respectively.

In order to evaluate procognitive activity of 3-Methyl-2-((2S)-2-(4-(5-methyl-1,2,4-oxadiazol-3-yl)phenyl)morpholino)-6-(pyrimidin-4-yl)pyrimidin-4(3H)-one on episodic memory deficits, mice were treated with the cholinergic antagonist scopolamine (1 mg/kg s.c.) 30 minutes before the acquisition phase. Scopolamine completely abolished episodic memory, treated mice did not remember the object explored 3 h before. A single oral administration of 3-methyl-2-((2S)-2-(4-(5-methyl-1,2,4-oxadiazol-3-yl)phenyl)morpholino)-6-(pyrimidin-4-yl)pyrimidin-4(3H)-one (10 mg/kg) 30 minutes before scopolamine treatment, i.e. 1 h before the acquisition phase, totally reversed the episodic memory deficits induced by scopolamine, the lower dose of 3 mg/kg being ineffective. RI values were 63.5%, 61.7%, and 59.7% in normal mice, and 49.9%, 52.7%, and 60.4% in scopolamine-treated mice, at 0, 10, 30 mg/kg, respectively.

Altogether, our behavioral results demonstrate that the TPK1 inhibitor 3-methyl-2-((2S)-2-(4-(5-methyl-1,2,4-oxadiazol-3-yl)phenyl)morpholino)-6-(pyrimidin-4-yl)pyrimidin-4(3H)-one increases episodic memory and consolidates episodic memory trace in normal mice at a minimal effective dose of 10 mg/kg. In addition, 3-methyl-2-((2S)-2-(4-(5-methyl-1,2,4-oxadiazol-3-yl)phenyl)morpholino)-6-(pyrimidin-4-yl)pyrimidin-4(3H)-one prevents episodic memory deficits in scopolamine-treated mice (MED 10 mg/kg). These behavioural data strongly support a procognitive potential for the 3-methyl-2-((2S)-2-(4-(5-methyl-1,2,4-oxadiazol-3-yl) phenyl)morpholino)-6-(pyrimidin-4-yl)pyrimidin-4(3H)-one.

Formulation Example (1) Tablets

The ingredients below were mixed by an ordinary method and compressed by using a conventional apparatus.

|  |  |
|---|---|
| Compound of the present invention (prepared in Preparation Example) | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

|  |  |
|---|---|
| Compound of the present invention (prepared in Preparation Example) | 30 mg |
| Olive oil | 300 mg |
| Lecithin | 20 mg |

Industrial Applicability

The compounds of the present invention have TPK1 inhibitory activity and are useful as an active ingredient of a medicament for preventive and/or therapeutic treatment of diseases caused by abnormal advance of TPK1 such as neurodegenerative diseases (e.g. Alzheimer disease) and the above-mentioned diseases.

The invention claimed is:

1. A compound represented by the formula (I) or a pharmaceutically acceptable salt thereof:

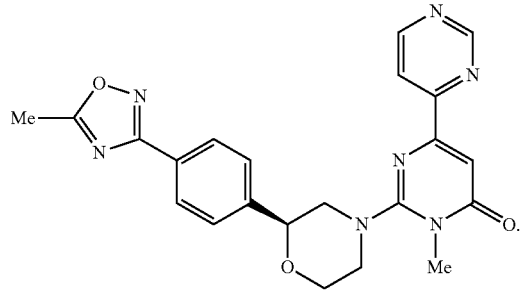

(I)

2. A medicament comprising as an active ingredient a substance selected from the group consisting of the compound represented by the formula (I) or a pharmaceutically acceptable salt thereof according to claim 1.

3. A tau protein kinase 1 inhibitor comprising as an active ingredient a substance selected from the group consisting of the compound represented by the formula (I) or a pharmaceutically acceptable salt thereof according to claim 1.

* * * * *